United States Patent
Kikuchi et al.

(10) Patent No.: US 6,596,706 B1
(45) Date of Patent: Jul. 22, 2003

(54) PIPERAZINE-CYCLODEXTRIN COMPLEXES

(75) Inventors: Masahiko Kikuchi, Tokyo (JP); Yukihiko Nagase, Tokyo (JP); Kaneto Uekama, Kumamoto (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/530,592

(22) PCT Filed: Oct. 29, 1998

(86) PCT No.: PCT/JP98/04896
§ 371 (c)(1),
(2), (4) Date: May 8, 2000

(87) PCT Pub. No.: WO99/24475
PCT Pub. Date: May 20, 1999

(30) Foreign Application Priority Data

Nov. 7, 1997 (JP) ............................................. 9-305889

(51) Int. Cl.[7] .................... A61K 31/724; A61K 31/497
(52) U.S. Cl. .............. 514/58; 514/252.12; 514/252.13; 514/255.03
(58) Field of Search ................. 514/252.12, 252.13, 514/255.03, 58

(56) References Cited

U.S. PATENT DOCUMENTS 5,376,645 A  * 12/1994 Stella et al. .................. 514/58

FOREIGN PATENT DOCUMENTS

| EP | 292050 | * 11/1988 |
| EP | 503710 | * 9/1992 |
| EP | 624584 | * 11/1994 |
| FR | 2 693 722 | 1/1994 |
| JP | 6-40890 | 2/1994 |
| JP | 6-153860 | 6/1994 |
| JP | 7-97364 | 4/1995 |
| WO | WO 85/02767 | 7/1985 |

OTHER PUBLICATIONS

Yamamoto, M., et al., "Biopharmaceutical evaluation of maltosyl–b–cyclodextrin as a parenteral drug carrier" S.T.P. Pharma Sci., 1991, vol 1, no 6, pp. 397–402.*

Karl–Heinz Frömming, et al., Arch. Pharm., vol. 320, No. 4, pp. 294–297, "Einschlubsserbindungen von Cyclodextrinen mit Piperazin", 1987.

* cited by examiner

*Primary Examiner*—Kathleen K. Ponda
*Assistant Examiner*—Leigh C. Maier
(74) *Attorney, Agent, or Firm*—Oblon, Spivak, McClelland, Maier & Neustadt, P.C.

(57) ABSTRACT

The present invention relates to a compound represented by formula (1):

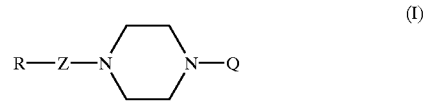

wherein Q, which may have a substituent, represents an aryl group, a heterocyclic group, a diarylmethyl group, or an aralkyl group; R, which may have a substituent, represents a bicyclic nitrogen-containing heterocyclic group or a phenyl group; and Z represents a C1–C3 alkylene group, a C2–C4 alkenylene group, a C1–C3 alkylene group having one hydroxyl group, a carbonyl moiety, a C1–C2 alkylene group containing one carbonyl moiety at one end or an intermediate position of the carbon chain, or an oxalyl group; or salts thereof and a piperazine-cyclodextrin complex combined with a water-soluble cyclodextrin derivative. The complex exhibits enhanced water solubility, excellent stability, and low topical stimulation and is useful as a therapeutic agent for circulatory diseases and diseases of the brain region.

19 Claims, 2 Drawing Sheets

PIPERAZINE-CYCLODEXTRIN COMPLEXES

This application is the National Stage filed under 35 USC 371 of PCT/JP98/04896, filed Oct. 29, 1998.

The present invention relates to a piperazine-cyclodextrin complex which exhibits enhanced water solubility, excellent stability, and low topical stimulation and is useful as a therapeutic agent for circulatory diseases and diseases of the brain region.

BACKGROUND ART

Piperazine derivatives represented by the below-described formula (I) have been known to exhibit calmodulin-inhibition and to be useful as therapeutic agents for circulatory diseases and diseases of the brain region (Japanese Patent Application Laid-Open (kokai) No. 7-97364).

However, due to their poor water solubility, the piperazine derivatives (I) are difficult to be incorporated into an injection formulation. Even though an injection formulation is prepared from the piperazine derivatives (I), when the content of the derivatives increases, the formulation tends to provide topical stimulation due to hemolysis activity and vascular permeability attributed to the piperazine derivatives. Furthermore, there has also been a problem that the formulation has relatively low stability against light and its active component thereof is adsorbed on the container, depending on the material of the container, to thereby reduce the efficacy.

Therefore, an object of the present invention is to provide a piperazine-cyclodextrin complex which exhibits enhanced water solubility, excellent stability, and low topical stimulation.

DISCLOSURE OF THE INVENTION

In the light of the foregoing, the present inventors have conducted earnest studies and have found that a piperazine-cyclodextrin complex formed of a piperazine derivative represented by the below-described formula (I) and a water-soluble cyclodextrin derivative exhibits enhanced water solubility, excellent stability, and low topical stimulation and is useful as a therapeutic agent for circulatory diseases and diseases of the brain region. The present invention was accomplished based on this finding.

Accordingly, the present invention provides a piperazine-cyclodextrin complex formed of a piperazine derivative or a salt thereof and a water-soluble cyclodextrin derivative, wherein the piperazine derivative is represented by formula (I):

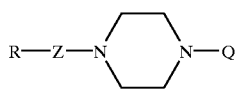
(I)

wherein Q represents (1) an aryl group,
(2) a heterocyclic group,
(3) a diarylmethyl group,
(4) an aralkyl group formed of an aryl group and a C1–C6 alkylene group,
(5) a C1–C8 alkyl group, or
(6) a C3–C8 cycloalkyl group, wherein each of the aryl group, the heterocyclic group, and the aryl groups in the diarylmethyl group and the aralkyl group may have one or more substituents selected from among the following groups:

1) a C1–C6 alkyl group,
2) a C1–C6 alkoxyl group,
3) a trifluoromethyl group and a 2,2,2-trifluoroethyl group,
4) a trifluoromethoxyl group and a 2,2,2-trifluoroethoxyl group,
5) a C1–C6 alkylthio group,
6) a C1–C6 alkylsulfinyl group,
7) a C1–C6 alkylsulfonyl group,
8) an alkanoyl group formed of a C1–C6 alkyl group and a carbonyl group,
9) a C2–C7 alkanoyloxy group,
10) a C2–C7 alkanoylamino group,
11) an amino group,
12) a monoalkylamino group having a C1–C6 alkyl group,
13) a dialkylamino group wherein each of the alkyl groups is a C1–C6 alkyl group,
14) a hydroxyl group,
15) a halogen atom,
16) a C2–C6 perfluoroalkyl group,
17) a cyano group,
18) a nitro group,
19) a carboxyl group,
20) an alkoxycarbonyl group formed of a C1–C6 alkoxyl group and a carbonyl group,
21) a tetrazolyl group,
22) a sulfamoyl group,
23) a methylenedioxy group, an ethylenedioxy group, and a propylenedioxy group,
24) a morpholinosulfonyl group,
25) a piperazinosulfonyl group,
26) a 4-alkylpiperazinosulfonyl group having a C1–C6 alkyl group,
27) a 4-(dialkylamino)piperidino group having a dialkylamino group having two C1–C6 alkyl groups which may be identical to or different from each other,
28) a 4-(monoalkylamino)piperidino group having a C1–C6 alkyl group, and
29) a 4-aminopiperidyl group;

R represents a bicyclic nitrogen-containing heterocyclic group (i) or a phenyl group (ii), wherein the nitrogen-containing heterocyclic group has a condensed ring structure formed of a 5-membered ring and a 6-membered ring; one or two nitrogen atoms are contained in the 5-membered ring portion; the nitrogen-containing ring may be an aromatic or saturated ring; and the saturated ring may contain a ketone moiety; wherein the 5-membered ring portion of the bicyclic heterocyclic group (i) or the phenyl group (ii) is substituted with substituent G selected from the group consisting of the following groups:

(aa) a C1–C6 alkyl group,
(ab) a phenyl group which may have a substituent,
(ac) a benzyl group which may have a substituent in the phenyl group portion,
(ad) a benzoyl group which may have a substituent in the phenyl group portion, (ae) a benzylcarbonyl group which may have a substituent in the phenyl group portion,
(af) a benzoylmethyl group which may have a substituent in the phenyl group portion,
(ag) an α-hydroxybenzyl group which may have a substituent in the phenyl group portion,
(ah) a 5-membered aromatic heterocyclic group which may have a substituent and which contains as a heteroatom a nitrogen atom, an oxygen atom, or a sulfur atom; wherein when the heteroatom is a nitrogen atom, the nitrogen atom is bonded to a hydrogen atom or to a C1–C6 alkyl group, or the nitrogen atom serves as the bonding site for the nitrogen-containing heterocyclic group or for the phenyl group,
(ai) a 5-membered aromatic heterocyclic group which may have a substituent and which contains as a heteroatom one nitrogen atom and as a second heteroatom a nitrogen atom, an oxygen atom, or a sulfur atom; wherein when the second heteroatom is a nitrogen atom, the nitrogen atom is bonded to a hydrogen atom or to a C1–C6 alkyl group, or the nitrogen atom serves as the bonding site for the nitrogen-containing heterocyclic group or for the phenyl group,
(aj) a 5-membered aromatic heterocyclic group which may have a substituent and which contains as heteroatoms two nitrogen atoms and as a third heteroatom a nitrogen atom, an oxygen atom, or a sulfur atom; wherein when the third heteroatom is a nitrogen atom, the nitrogen atom is bonded to a hydrogen atom or to a C1–C6 alkyl group, or the nitrogen atom serves as the bonding site for the nitrogen-containing heterocyclic group or for the phenyl group,
(ak) a 6-membered aromatic heterocyclic group which may have a substituent and which contains one or two nitrogen atoms,
(al) a heterocyclic group-substituted alkyl group formed of a C1–C3 alkylene group and a 5-membered aromatic heterocyclic group, which may have a substituent and contains as a heteroatom a nitrogen atom, an oxygen atom, or a sulfur atom; wherein when the heteroatom is a nitrogen atom, the nitrogen atom is bonded to a hydrogen atom or to a C1–C6 alkyl group,
(am) a heterocyclic group-substituted alkyl group formed of a C1–C3 alkylene group and a 5-membered aromatic heterocyclic group, which may have a substituent and contains as a heteroatom one nitrogen atom and as a second heteroatom a nitrogen atom, an oxygen atom, or a sulfur atom; wherein when the second heteroatom is a nitrogen atom, the nitrogen atom is bonded to a hydrogen atom or to a C1–C6 alkyl group, or the nitrogen atom serves as the bonding site for the alkylene group,
(an) a heterocyclic group-substituted alkyl group formed of a C1–C3 alkylene group and a 5-membered aromatic heterocyclic group, which 5-membered aromatic heterocyclic group may have a substituent and contains as heteroatoms two nitrogen atoms and as a third heteroatom a nitrogen atom, an oxygen atom, or a sulfur atom; wherein when the third heteroatom is a nitrogen atom, the nitrogen atom is bonded to a hydrogen atom or to a C1–C6 alkyl group, or the nitrogen atom serves as the bonding site for the alkylene group,
(ao) a heterocyclic group-substituted alkyl group formed of a C1–C3 alkylene group and a 6-membered aromatic heterocyclic group which may have a substituent and which contains one or two nitrogen atoms,
(ap) a phenylhydroxyalkyl group formed of a C2–C3 alkylene group having one hydroxyl group and a phenyl group which may have a substituent,
(aq) a 2-phenylethynyl group wherein its phenyl group may have a substituent,
(ar) a tetrazolyl group,
(as) a morpholino group,
(at) a C2–C7 alkanoylamino group,
(au) a tetrazolylalkyl group formed of a tetrazolyl group and a C1–C3 alkylene group wherein the alkylene group is bonded to the carbon atom or a nitrogen atom of the tetrazolyl group,
(av) a morpholinoalkyl group formed of a morpholino group and a C1–C3 alkylene group,
(aw) a 4-alkoxycarbonylcyclohexyl group wherein its alkoxyl group has one to six carbon atoms,
(ax) an alkoxycarbonyl group wherein its alkoxyl group has one to six carbon atoms,
(ay) an alkoxycarbonylalkyl group formed of a C1–C3 alkylene group and an alkoxycarbonyl group wherein its alkoxyl group has one to six carbon atoms,
(az) an 1-alkylindol-2-yl group wherein its alkyl group has one to six carbon atoms and the indole group may further have a substituent,
(ba) a pyrrolidon-1-yl group,
(bb) a 2-guanidinothiazolyl group,
(bc) a (2-guanidinothiazolyl)-alkyl group formed of a 2-guanidinothiazolyl group and a C1–C3 alkylene group,
(bd) a 1,4-dihydropyridyl group which may have a substituent,
(be) a 4-alkylpiperadinoalkyl group formed of a C1–C6 alkylene group and a 4-alkylpiperazino group having a C1–C6 alkyl group,
(bf) a 4-(morpholinosulfonyl)phenylalkyl group formed of a 4-(morpholinosulfonyl)phenyl group and a C1–C6 alkylene group,
(bg) a 4-(piperazinosulfonyl)phenylalkyl group formed of a 4-(piperazinosulfonyl)phenyl group and a C1–C6 alkylene group,
(bh) a 4-(piperazinosulfonyl)phenylalkyl group formed of a C1–C6 alkylene group and a 4-(4-alkylpiperazinosulfonyl)phenyl group having a C1–C6 alkyl group,
(bi) an alkoxycarbonylalkyl group formed of a C2–C7 alkoxycarbonyl group and a C1–C6 alkylene group,
(bj) a carboxylalkyl group formed of a carboxyl group and a C1–C6 alkylene group,
(bk) a [4-(4-dialkylaminopiperidino)phenyl]alkyl group formed of a C1–C6 alkylene group and a 4-(4-dialkylaminopiperidino)phenyl group wherein a 4-dialkylaminopiperidino group having, at the 4-position of the piperidine, a dialkylamino group containing two C1–C6 alkyl groups is bonded to the 4-position of the phenyl group,
(bl) a 4-(4-monoalkylaminopiperidino)phenylalkyl group formed of a C1–C6 alkylene group and a 4-(4-monoalkylaminopiperidino)phenyl group wherein a 4-monoalkylaminopiperidino group having, at the 4-position of the piperidine, a monoalkylamino group containing a C1–C6 alkyl group is bonded to the 4-position of the phenyl group,
(bm) a [4-(4-aminopiperidino)phenyl]alkyl group formed of a C1–C6 alkylene group and a 4-(4- aminopiperidino)phenyl group wherein a 4-aminopiperidino group is bonded to the 4-position of the phenyl group, (bn) a (4-dialkylaminopiperidino)alkyl group formed of a C1–C6 alkylene group and a 4-dialkylaminopiperidino group wherein a dialkylamino group having two C1–C6 alkyl groups is bonded to the 4-position of the piperidine, (bo) a (4-monoalkylaminopiperidino)alkyl group formed of a C1–C6 alkylene group and a 4-monoalkylaminopiperidino group wherein a monoalkylamino group having a C1–C6 alkyl group is bonded to the 4-position of the piperidine, (bp) a (4-aminopiperidino)alkyl group formed of a 4-aminopiperidino group and a C1–C6 alkylene group, and (bq) a hydrogen atom, wherein when the substituents represented by (aa) through (ap) have substituents, the substituents are one or more members selected from the group consisting of the following substituents:

1) a C1–C6 alkyl group,
2) a C1–C6 alkoxyl group,
3) a trifluoromethyl group and a 2,2,2-trifluoroethyl group,
4) a trifluoromethoxyl group and a 2,2,2-trifluoroethoxyl group,
5) a C1–C6 alkylthio group,
6) a C1–C6 alkylsulfinyl group,
7) a C1–C6 alkylsulfonyl group,
8) an alkanoyl group formed of a C1–C6 alkyl group and a carbonyl group,
9) a C2–C7 alkanoyloxy group,
10) a C2–C7 alkanoylamino group,
11) an amino group,
12) a monoalkylamino group having a C1–C6 alkyl group,
13) a dialkylamino group wherein each of the alkyl groups is a C1–C6 alkyl group,
14) a hydroxyl group,
15) a halogen atom,
16) a C2–C6 perfluoroalkyl group,
17) a cyano group,
18) a nitro group,
19) a carboxyl group,
20) an alkoxycarbonyl group formed of a C1–C6 alkoxyl group and a carbonyl group,
21) a tetrazolyl group,
22) a sulfamoyl group,
23) a methylenedioxy group, an ethylenedioxy group, and a propylenedioxy group,
24) a morpholinosulfonyl group,
25) a piperazinosulfonyl group,
26) a 4-alkylpiperazinosulfonyl group having a C1–C6 alkyl group,
27) a 4-(dialkylamino)piperadino group having a dialkylamino group having two C1–C6 alkyl groups which may be identical to or different from each other,
28) a 4-(monoalkylamino)piperidino group having a C1–C6 alkyl group, and
29) a 4-aminopiperidino group;

wherein the 6-membered ring portion of the bicyclic heterocyclic group (i) or the phenyl group (ii) may have one or more groups selected from among a C1–C6 alkyl group, a C1–C6 alkoxyl group, a trifluoromethyl group, a 2,2,2-trifluoroethyl group, a trifluoromethoxyl group, a 2,2,2-trifluoroethoxyl group, a C1–C6 alkylthio group, a C1–C6 alkylsulfinyl group, a C1–C6 alkylsulfonyl group, an alkanoyl group formed of a C1–C6 alkylene group and a carbonyl group, a C2–C7 alkanoyloxy group, a C2–C7 alkanoylamino group, an amino group, a monoalkylamino group having a C1–C6 alkyl groups, a dialkylamino group having two C1–C6 alkyl groups which may be identical to or different from each other, a hydroxyl group, a halogen atom, a C2–C6 perfluoroalkyl group, a cyano group, a nitro group, a carboxyl group, an alkoxycarbonyl group formed of a C1–C6 alkoxyl group and a carbonyl group, a tetrazolyl group, a sulfamoyl group, a methylenedioxy group, an ethylenedioxy group, a morpholinosulfonyl group, a piperazinosulfonyl group, a 4-alkylpiperazinosulfonyl group having a C1–C6 alkyl group, a 4-dialkylaminopiperidino group having at the 4-position a dialkylamino group having two C1–C6 alkyl groups which may be identical to or different from each other, a 4-monoalkylaminopiperidino group having a C1–C6 alkyl group, or a 4-aminopiperidino group; and Z represents (1) a C1–C3 alkylene group,
(2) a C2–C4 alkenylene group,
(3) a C1–C3 alkylene group having one hydroxyl group,
(4) a carbonyl moiety,
(5) a C1–C2 alkylene group containing one carbonyl moiety at one end or an intermediate position of the carbon chain, or
(6) an oxalyl group.

The present invention also provides an injection formulation containing the piperazine-cyclodextrin complex.

The present invention also provides a therapeutic agent for circulatory diseases, a therapeutic agent for brain diseases, and a brain protecting agent containing the piperazine-cyclodextrin complex as an active component.

The present invention further provides use of the piperazine-cyclodextrin complex as a pharmaceutical.

The present invention still further provides a method for treatment of circulatory diseases and brain diseases, characterized by administration of the piperazine-cyclodextrin complex.

BEST MODES FOR CARRYING OUT THE INVENTION

Figure 1:
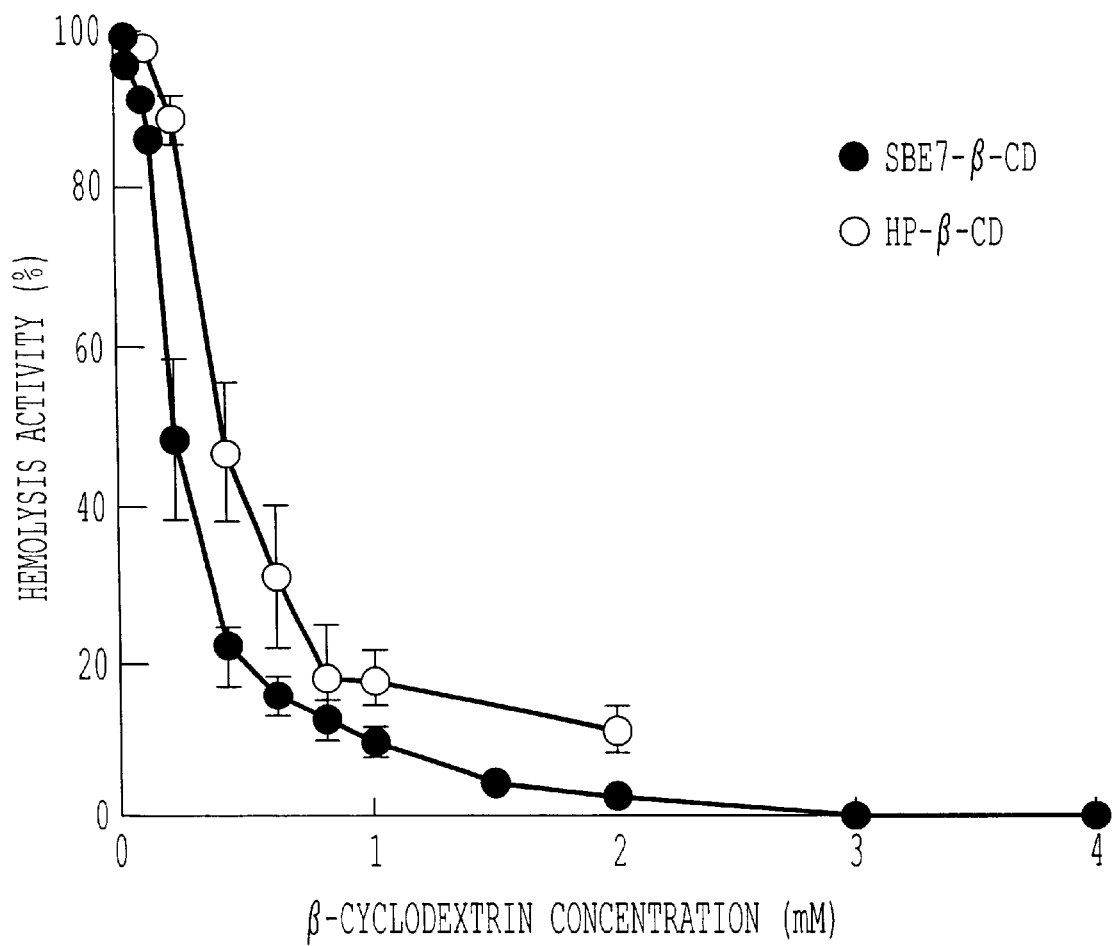
FIG. 1 is a graph showing the hemolysis activity data obtained in Example 2, in which β-cyclodextrin was added at a variety of concentrations.

The piperazine derivative which is used in the present invention is represented by the above-described formula (I), and has a partial structure represented by Q connecting to one nitrogen atom of piperazine and a partial structure represented by R connecting to the other nitrogen atom via a linkage portion Z.

The partial structure Q represents a substituent selected from among (1) an aryl group, (2) a heterocyclic group, (3) a diarylmethyl group, (4) an aralkyl group formed of an aryl group and a C1–C6 alkylene group, (5) a C1–C8 alkyl group, or (6) a C3–C8 cycloalkyl group.

An aryl group is a substituent derived from an aromatic compound, and typical examples include a phenyl group and a naphthyl group. Although aromatic compounds also include heterocyclic compounds, the aryl group in the present invention refers particularly to a substituent derived from an aromatic hydrocarbon compound.

A heterocyclic group is a substituent derived from a heterocyclic compound. Among heterocyclic compounds, nitrogen-containing heterocyclic compounds are preferred in the present invention. There are several types of nitrogen-containing heterocyclic compounds such as aromatic, partially saturated, and saturated species. Of these, aromatic heterocyclic compounds are preferred. Examples of the nitrogen-containing aromatic heterocyclic compounds includes pyrrole, imidazole, pyrazole, pyridine, pyridazine, pyrimidine, pyrazine, indole, quinoline, isoquinoline, cinnoline, phthalazine, quinazoline, quinoxaline, naphthyridine, pyridopyridines, carbazole, carboline, phenanthridine, and acrydine. The compounds of the present invention may have a substituent derived from these heterocyclic compounds. Among these substituents, a pyridyl group, a pyrimidyl group, and an isoquinolyl group are preferred.

In addition to nitrogen-containing heterocyclic groups, there may be used heterocyclic groups containing an oxygen atom or a sulfur atom. In this case, the heterocyclic compounds may be aromatic, partially saturated, or saturated. For example, thienyl, benzothienyl, furyl, furanyl, benzofuranyl, or chromenyl may be used. Of these, a group such as a benzofuranyl group or a dihydrobenzofuranyl group is preferred.

Yet other than these groups, there may also be used a heterocyclic substituent containing a plurality of heteroatom species such as isothiazolyl, isoxazolyl, or oxazinyl.

The diarylmethyl group is a substituent in which two hydrogen atoms of the methyl group are substituted with two aryl groups. The aryl groups may be those as described above. The most typical diarylmethyl group is a diphenyl-methyl group.

The aralkyl group formed of an aryl group and a C1–C6 alkylene group is a substituent in which one end of the alkylene group is bonded to the above-described aryl group. Typical examples include a benzyl group and a phenethyl group.

The alkyl group may be a linear or branched C1–C8 alkyl group.

The cycloalkyl group may have 3–8 carbon atoms, and examples thereof include a cyclopropyl group, a cyclobutyl group, a cyclopentyl group, a cyclohexyl group, and a cyclooctyl group.

Each of the above-described aryl groups, heterocyclic groups, diarylmethyl groups, C1–C8 alkyl groups, C3–C8 cycloalkyl groups, and aralkyl groups formed of an aryl group and a C1–C6 alkylene group may be substituted with a variety of substituents. In particular, the aryl groups, the heterocyclic groups, and the aryl groups of the arylmethyl groups may have a substituent. The substituents are selected from the following group consisting of substituents 1) through 29) below:

1) a C1–C6 alkyl group, which may be liner or branched and may be a cycloalkyl group when it has three or more carbon atoms;
2) a C1–C6 alkoxyl group, which may be formed of the above alkyl group and an oxygen atom, i.e., its alkyl moiety may be linear, branched or cyclic;
3) a trifluoromethyl group and a 2,2,2-trifluoroethyl group;
4) a trifluoromethoxyl group and a 2,2,2-trifluoroethoxyl group;
5) an alkylthio group, which may be formed of the above C1–C6 alkyl group and a sulfur atom and has an "alkyl-S—" structure, wherein its alkyl moiety may be linear, branched or cyclic;
6) an alkylsulfinyl group, which is a substituent obtained through oxidation of the sulfur atom of the above alkylthio group by one oxygen atom and has an "alkyl-SO—" structure;
7) an alkylsulfonyl group, which is a substituent obtained through oxidation of the sulfur atom of the above alkylthio group by two oxygen atoms and has an "alkyl-SO$_2$—" structure;
8) an alkanoyl group, which is a substituent produced by removing a hydroxyl group from a carboxylic acid moiety of an aliphatic carboxylic acid and has an "alkyl-CO—" structure;
9) an alkanoyloxy group, which is a substituent having a structure of the above alkanoyl group to which an oxygen atom is added or a structure of a carboxylic acid moiety of an aliphatic carboxylic acid from which a hydrogen atom is removed, i.e., which alkanoyloxy group has an "alkyl-CO—O—" structure;
10) an alkanoylamino group, which has a structure in which one of the two hydrogen atoms of its amino group is substituted with an alkanoyl group, i.e., an "alkyl-CO—NH—" structure;
11) an amino group;
12) a monoalkylamino group, which has a structure in which one of the two hydrogen atoms of its amino group is substituted with an alkyl group, and 13) a dialkylamino group, which has a structure in which both of the two hydrogen atoms of its amino group are substituted with an alkyl group;
14) a hydroxyl group;
15) a halogen atom;
16) a perfluoroalkyl group, which has a structure in which all hydrogen atoms in its alkyl group are substituted, with a fluorine atom and has a linear, a branched, or a cyclic structure;
17) a cyano group;
18) a nitro group;
19) a carboxyl group;
20) an alkoxycarbonyl group wherein its alkyl group and its carbonyl group are linked via an oxygen atom and its alkyl moiety may has a linear, a branched, or a cyclic structure, i.e., the alkoxycarbonyl group has an "alkyl-O—CO—" structure;
21) a tetrazolyl group, which is a 5-membered heterocyclic group;
22) a sulfamoyl group;
23) each of a methylenedioxy group, an ethylenedioxy group, and a propylenedioxy group has an —O—(CH$_2$)$_q$—O—structure wherein q represents a number between 1 and 3 inclusive and two carbon atoms connecting with oxygen atoms are linked adjacently;
24) a morpholinosulfonyl group, which has a structure represented by "morpholino (i.e., 4-morphonyl group)-SO$_2$—";
25) a piperazinosulfonyl group, which has a structure represented by "(1-piperazinyl)-SO$_2$—";

26) a 4-alkylpiperazinosulfonyl group, which has a structure represented by "(4-alkyl-1-piperazinyl)-$SO_2$—" wherein the alkyl group connecting with the 4-position of the piperazinyl group is a C1–C6 alkyl group;

27) a 4-(dialkylamino)piperidino group, which has a structure represented by "4-dialkylamino-1-piperidinyl" wherein the dialkylamino group connecting with the 4-position of the piperazinyl group has two C1–C6 alkyl groups which may be identical to or different from each other;

28) a 4-(monoalkylamino)piperidino group, which has a structure represented by "4-monoalkylamino-1-piperidinyl" wherein the monoalkylamino group connecting with the 4-position of the piperazinyl group has a C1–C6 alkyl group; and 29) a 4-aminopiperidino group, which has an amino group at the 4-position of the piperidinyl group.

One or more substituents may be selected from the group consisting of the above substituents. When two substituents are chosen, the substituents may be of a single species or a plurality of species.

Furthermore, the substituent selected from the group of the substituents may be bonded to the alkyl group or the cycloalkyl group of the substituents included in Q.

To the other nitrogen atom in the piperazine ring of the piperazine derivative (I), the moiety R of a bicyclic nitrogen-containing heterocyclic group (1) or a phenyl group (2) is bonded via a linkage moiety Z selected from among (1) a C1–C3 alkylene group, (2) a C2–C4 alkenylene group, (3) a C1–C3 alkylene group having one hydroxyl group, (4) a carbonyl moiety, (5) a C1–C2 alkylene group containing one carbonyl moiety at one end or an intermediate position of the carbon chain, or (6) an oxalyl group.

The alkylene group forming the moiety Z has the below-described formula:

wherein r represents a number between 1 and 3 inclusive. The alkenylene group is a C2–C4 alkenylene group in which one carbon-carbon bond is a double bond which may exist at an end or an intermediate position.

The C1–C3 alkylene group having one hydroxyl group is a C1–C3 alkylene group in which one carbon atom has a hydroxyl group. No limitation is imposed on the position of the hydroxyl group, and it may exist at an end or an intermediate position.

The carbonyl moiety (or carbonyl group) has a structure represented by "—CO—."

The C1–C2 alkylene group containing one carbonyl moiety at one end or an intermediate position of the carbon chain has one of the following structures:

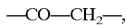

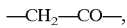

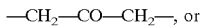

The oxalyl group has a structure of "—CO—CO—."

The partial structure represented by R comprises a bicyclic nitrogen-containing heterocyclic group (i) or a phenyl group (ii).

Of the two groups, the bicyclic heterocyclic group has structural characteristics that (1) it has a condensed ring structure formed of a 5-membered ring and a 6-membered ring; (2) one or two nitrogen atoms are contained in the 5-membered ring portion; (3) the nitrogen-containing ring may be an aromatic or saturated ring; and (4) the saturated ring may contain a ketone moiety.

Specifically, the heterocyclic group is a group derived from indole, isoindole, indazole, or benzo[d]imidazole. Also, mention may be given of groups derived from heterocyclic compounds containing an internuclear nitrogen atom, such as indolidine, benzo[a]pyrazole, benzo[e]pyrazole, benzo[a]imidazole, or benzo[e]imidazole. The hetrocyclic substituents are bonded to the above-mentioned linkage portion Z via a nitrogen atom or a carbon atom of the 5-membered ring.

More specific examples of such heterocyclic substituents include indol-1-yl, indol-2-yl, indol-3-yl, 2,3-dihydroindol-1-yl, 2,3-dihydroindol-2-yl, 2,3-dihydroindol-3-yl, 3H-indol-2-yl, 3H-indol-3-yl, 2-oxoindol-1-yl, 2-oxoindol-3-yl, indazol-1-yl, indazol-3-yl, 2,3-dihydroindazol-1-yl, 2,3-dihydroindazol-2-yl, 2,3-dihydroindazol-3-yl, 3H-indazol-3-yl, 2,3-dihydro-3-oxoindazol-1-yl, 2,3-dihydro-3-oxoindazol-2-yl, isoindol-1-yl, isoindol-2-yl, isoindol-3-yl, 1,3-dihydroisoindol-1-yl, 1,3-dihydroisoindol-2-yl, 1,3-dihydroisoindol-3-yl, 1,3-dihydro-3-oxoisoindol-1-yl, 1,3-dihydro-3-oxoisoindol-2-yl, 1,3-dihydro-1-oxoisoindol-2-yl, 1,3-dihydro-1-oxoisoindol-3-yl, benzo[d]imidazol-1-yl, benzo[d]imidazol-2-yl, 2,3-dihydrobenzo[d]imidazol-1-yl, 2,3-dihydrobenzo[d]imidazol-2-yl, and 2,3-dihydro-2-oxobenzo[d]imidazol-1-yl.

The bicyclic nitrogen-containing heterocyclic group or the phenyl group, which is the partial structure represented by R, is substituted with substituent G selected from the group consisting of the following groups. When R is a phenyl group, a particularly preferable substitution site is a carbon atom adjacent to the carbon atom connecting with the moiety Z, i.e. an ortho position. When the portion R is a heterocyclic substituent, a preferable substitution site is in the nitrogen-containing 5-membered ring portion. In this case, the site may be a nitrogen atom or a carbon atom.

(aa) a C1–C6 alkyl group, which may be cyclic, linear, or branched;

(ab) a phenyl group which may have a substituent;

(ac) a benzyl group which may have a substituent in the phenyl group portion;

(ad) a benzoyl group which may have a substituent in the phenyl group portion;

(ae) a benzylcarbonyl group which may have a substituent in the phenyl group portion;

(af) a benzoylmethyl group which may have a substituent in the phenyl group portion;

(ag) an α-hydroxybenzyl group which may have a substituent in the phenyl group portion;

(ah) a 5-membered aromatic heterocyclic group which may have a substituent and which contains as a heteroatom a nitrogen atom, an oxygen atom, or a sulfur atom; wherein when the heteroatom is a nitrogen atom, the nitrogen atom is bonded to a hydrogen atom or to a C1–C6 alkyl group, or the nitrogen atom serves as the bonding site for the nitrogen-containing heterocyclic group or for the phenyl group, examples of the 5-membered aromatic heterocyclic group including a pyrrolyl group, a furyl group, and a thienyl group. This substituent may be bonded to the bicyclic nitrogen-containing heterocyclic group or phenyl group at any of possible sites thereof;

(ai) a 5-membered aromatic heterocyclic group which may have a substituent and which contains as a heteroatom one nitrogen atom and as a second heteroatom a nitrogen atom, an oxygen atom, or a sulfur atom; wherein when the second heteroatom is a nitrogen atom, the nitrogen atom is bonded to a hydrogen atom or to a C1–C6 alkyl group, or the nitrogen atom serves as the bonding site for the nitrogen-containing heterocyclic group or for the phenyl group, examples of the 5-membered aromatic heterocyclic group including a pyrazolyl group, a imidazolyl group, a thiazolyl group, an isothiazolyl group, an oxazolyl group, and an isoxazolyl group. This substituent may be bonded to the bicyclic nitrogen-containing heterocyclic group or phenyl group at any of possible sites thereof;

(aj) a 5-membered aromatic heterocyclic group which may have a substituent and which contains as heteroatoms two nitrogen atoms and as a third heteroatom a nitrogen atom, an oxygen atom, or a sulfur atom; wherein when the third heteroatom is a nitrogen atom, the nitrogen atom is bonded to a hydrogen atom or to a C1–C6 alkyl group, or the nitrogen atom serves as the bonding site for the nitrogen-containing bicyclic heterocyclic group or for the phenyl group, examples of the 5-membered aromatic heterocyclic group including a 1,2,3-triazolyl group, a 1,2,4-triazolyl group, a 1,2,3-thiadiazyl group, a 1,2,4-thiadiazyl group, a 1,2,5-thiadiazyl group, a 1,3,4-thiadiazyl group, a 1,2,3-oxadiazyl group, a 1,2,4-oxadiazyl group, a 1,2,5-oxadiazyl group, and a 1,3,4-oxadiazyl group. This substituent may be bonded to the bicyclic nitrogen-containing heterocyclic group or phenyl group at any of possible sites thereof;

(ak) a 6-membered aromatic heterocyclic group which may have a substituent and which contains one or two nitrogen atoms, examples of the 6-membered aromatic heterocyclic group including a pyridyl group, a pyridazinyl group, a pyrimidyl group, and a piradinyl group. This substituent may be bonded to the bicyclic nitrogen-containing heterocyclic group or phenyl group at any of possible sites thereof;

(al) a heterocyclic group-substituted alkyl group formed of a C1–C3 alkylene group and a 5-membered aromatic heterocyclic group, which 5-membered aromatic heterocyclic group may have a substituent and contains as a heteroatom a nitrogen atom, an oxygen atom, or a sulfur atom; wherein when the heteroatom is a nitrogen atom, the nitrogen atom is bonded to a hydrogen atom or to a C1–C6 alkyl group, examples of the heterocyclic group-substituted alkyl group including a pyrrolyl-methyl-ethyl or propyl group, a thienyl-methyl-ethyl or propyl group, and a furyl-methyl, ethyl or propyl group, wherein the alkylene group may be bonded to any possible bonding site of the heterocyclic moiety;

(am) a heterocyclic group-substituted alkyl group formed of a C1–C3 alkylene group and a 5-membered aromatic heterocyclic group, which 5-membered aromatic heterocyclic group may have a substituent and contains as a heteroatom one nitrogen atom and as a second heteroatom a nitrogen atom, an oxygen atom, or a sulfur atom; wherein when the second heteroatom is a nitrogen atom, the nitrogen atom is bonded to a hydrogen atom or to a C1–C6 alkyl group, or the nitrogen atom serves as the bonding site for the alkylene group, examples of the heterocyclic group-substituted alkyl group including a pyrazolyl-methyl, ethyl, or propyl group, an imidazolyl-methyl, ethyl, or propyl group, a thiazolyl-methyl, ethyl, or propyl group, and an oxazolyl-methyl, ethyl or propyl group, wherein the alkylene group may be bonded to any possible bonding site of the heterocyclic moiety;

(an) a heterocyclic group-substituted alkyl group formed of a C1–C3 alkylene group and a 5-membered aromatic heterocyclic group, which 5-membered aromatic heterocyclic group may have a substituent and contains as heteroatoms two nitrogen atoms and as a third heteroatom a nitrogen atom, an oxygen atom, or a sulfur atom; wherein when the third heteroatom is a nitrogen atom, the nitrogen atom is bonded to a hydrogen atom or to a C1–C6 alkyl group, or the nitrogen atom serves as the bonding site for the alkylene group, examples of the heterocyclic group-substituted alkyl group including a 1,2,3-triazolyl-methyl, ethyl, or propyl group, a 1,2,4-triazolyl-methyl, ethyl, or propyl group, a 1,2,3-thiadiazyl-methyl, ethyl, or propyl group, a 1,2,4-thiadiazyl-methyl, ethyl, or propyl group, a 1,2,5-thiadiazyl-methyl, ethyl, or propyl group, a 1,3,4-thiadiazyl-methyl, ethyl, or propyl group, a 1,2,3-oxadiazyl-methyl, ethyl, or propyl group, a 1,2,4-oxadiazyl-methyl, ethyl, or propyl group, a 1,2,5-oxadiazyl-methyl, ethyl, or propyl group, and a 1,3,4-oxadiazyl-methyl, ethyl, or propyl group, wherein the alkylene group may be bonded to any possible bonding site of the heterocyclic moiety;

(ao) a heterocyclic group-substituted alkyl group formed of a C1–C3 alkylene group and a 6-membered aromatic heterocyclic group which may have a substituent and which contains one or two nitrogen atoms, examples of the 6-membered aromatic heterocyclic group including a pyridyl-methyl, ethyl, or propyl group, a pyridazinyl-methyl, ethyl, or propyl group, a pyrimidyl-methyl, ethyl, or propyl group, and a piradinyl-methyl, ethyl, or propyl group wherein the alkylene group may be bonded to any possible bonding site of the heterocyclic moiety;

(ap) a phenylhydroxyalkyl group formed of a C2–C3 alkylene group having one hydroxyl group and a phenyl group which may have a substituent, examples thereof including a 1-hydroxy-2-phenylethyl group, a 2-hydroxy-2-phenylethyl, 1-hydroxy-3-phenylpropyl group, a 2-hydroxy-3-phenylpropyl group, and a 3-hydroxy-3-phenylpropyl group;

(aq) a 2-phenylethynyl group wherein its phenyl group may have a substituent;

(ar) a tetrazolyl group;

(as) a morpholino group;

(at) a C2–C7 alkanoylamino group;

(au) a tetrazolylalkyl group formed of a tetrazolyl group and a C1–C3 alkylene group wherein the alkylene group is bonded to the carbon atom or a nitrogen atom of the tetrazolyl group, examples thereof including a tetrazolyl-methy, ethyl, or propyl group;

(av) a morpholinoalkyl group formed of a morpholino group and a C1–C3 alkylene group, examples thereof including a morpholino-methy, ethyl, or propyl group;

(aw) an alkoxycarbonylcyclohexyl group wherein its alkoxyl group has one to six carbon atoms; the bonding site between the alkoxycarbonyl group and the 1-position may be a trans or a cis manner or may be an axial bond or an equatrial bond;

(ax) an alkoxycarbonyl group wherein its alkoxyl group has one to six carbon atoms;

(ay) an alkoxycarbonylalkyl group formed of a C1–C3 alkylene group and an alkoxycarbonyl group wherein its alkoxyl group has one to six carbon atoms, examples thereof including an alkoxycarbonyl-methy, ethyl, or propyl group;

(az) an 1-alkylindol-2-yl group wherein its alkyl group has one to six carbon atoms and the indole group may further have a substituent;

(ba) a pyrrolidon-1-yl group wherein an oxygen atom occupies the 2- or 3- position;

(bb) a 2-guanidinothiazolyl group;

(bc) a (2-guanidinothiazolyl)-alkyl group formed of a 2-guanidinothiazolyl group and a C1–C3 alkylene group;

(bd) a 1,4-dihydropyridyl group which may have a substituent such as alkyl groups and carboxyl groups, examples thereof including a 2,6-bis(methoxycarbonyl)-3,5-dimethyl-1,4-dihydropyridyl group;

(be) a 4-alkylpiperadinoalkyl group formed of a C1–C6 alkylene group and a 4-alkylpiperazino group having a C1–C6 alkyl group;

(bf) a 4-(morpholinosulfonyl)phenylalkyl group formed of a 4-(morpholinosulfonyl)phenyl group and a C1–C6 alkylene group;

(bg) a 4-(piperazinosulfonyl)phenylalkyl group formed of a 4-(piperazinosulfonyl)phenyl group and a C1–C6 alkylene group;

(bh) a 4-(piperazinosulfonyl)phenylalkyl group formed of a C1–C6 alkylene group and a 4-(4-alkylpiperazinosulfonyl)phenyl group having a C1–C6 alkyl group;

(bi) an alkoxycarbonylalkyl group formed of a C2–C7 alkoxycarbonyl group and a C1–C6 alkylene group;

(bj) a carboxylalkyl group formed of a carboxyl group and a C1–C6 alkylene group;

(bk) a [4-(4-dialkylaminopiperidino)phenyl]alkyl group formed of a C1–C6 alkylene group and a 4-(4-dialkylaminopiperidino)phenyl group wherein a 4-dialkylaminopiperidino group having, at the 4-position of the piperidine, a dialkylamino group containing two C1–C6 alkyl groups is bonded to the 4-position of the phenyl group;

(bl) a 4-(4-monoalkylaminopiperidino)phenylalkyl group formed of a C1–C6 alkylene group and a 4-(4-monoalkylaminopiperidino)phenyl group wherein a 4-monoalkylaminopiperidino group having, at the 4-position of the piperidine, a monoalkylamino group containing a C1–C6 alkyl group is bonded to the 4-position of the phenyl group;

(bm) a [4-(4-aminopiperidino)phenyl]alkyl group formed of a C1–C6 alkylene group and a 4-(4-aminopiperidino)phenyl group wherein a 4-aminopiperidino group is bonded to the 4-position of the phenyl group;

(bn) a (4-dialkylaminopiperidino)alkyl group formed of a C1–C6 alkylene group and a 4-dialkylaminopiperidino group wherein a dialkylamino group having two C1–C6 alkyl groups is bonded to the 4-position of the piperidine;

(bo) a (4-monoalkylaminopiperidino)alkyl group formed of a C1–C6 alkylene group and a 4-monoalkylaminopiperidino group wherein a monoalkylamino group having a C1–C6 alkyl group is bonded to the 4-position of the piperidine;

(bp) a (4-aminopiperidino)alkyl group formed of a 4-aminopiperidino group and a C1–C6 alkylene group; and (bq) a hydrogen atom.

With regard to the substituents listed in the above substituent group, the description "which may be substituted" or "which may have a substituent" refers to that the substituent may have a substituent selected from among the below-described substituent group. One or more substituents may be selected from the group consisting of the below-described substituents:

1) a C1–C6 alkyl group,
2) a C1–C6 alkoxyl group,
3) a trifluoromethyl group and a 2,2,2-trifluoroethyl group,
4) a trifluoromethoxyl group and a 2,2,2-trifluoroethoxyl group,
5) a C1–C6 alkylthio group,
6) a C1–C6 alkylsulfinyl group,
7) a C1–C6 alkylsulfonyl group,
8) an alkanoyl group formed of a C1–C6 alkyl group and a carbonyl group,
9) a C2–C7 alkanoyloxy group,
10) a C2–C7 alkanoylamino group,
11) an amino group,
12) a monoalkylamino group having a C1–C6 alkyl group,
13) a dialkylamino group wherein each of the alkyl groups is a C1–C6 alkyl group,
14) a hydroxyl group,
15) a halogen atom,
16) a C2–C6 perfluoroalkyl group,
17) a cyano group,
18) a nitro group,
19) a carboxyl group,
20) an alkoxycarbonyl group formed of a C1–C6 alkoxyl group and a carbonyl group,
21) a tetrazolyl group,
22) a sulfamoyl group,
23) a methylenedioxy group, an ethylenedioxy group, and a propylenedioxy group,
24) a morpholinosulfonyl group,
25) a piperazinosulfonyl group,
26) a 4-alkylpiperazinosulfonyl group having a C1–C6 alkyl group,
27) a 4-(dialkylamino)piperidino group having a dialkylamino group having two C1–C6 alkyl groups which may be identical to or different from each other,
28) a 4-(monoalkylamino)piperidino group having a C1–C6 alkyl group, and
29) a 4-aminopiperidino group. When two substituents are chosen, they may be of a single species or a plurality of species.

The 6-membered ring portion of the bicyclic heterocyclic group (i) or the phenyl group (ii) may have one or more groups selected from among a C1–C6 alkyl group, a C1–C6 alkoxyl group, a trifluoromethyl group, a 2,2,2-trifluoroethyl group, a trifluoromethoxyl group, a 2,2,2-trifluoroethoxyl group, a C1–C6 alkylthio group, a C1–C6 alkylsulfinyl group, a C1–C6 alkylsulfonyl group, an alkanoyl group formed of a C1–C6 alkylene group and a carbonyl group, a C2–C7 alkanoyloxy group, a C2–C7 alkanoylamino group, an amino group, a monoalkylamino group having a C1–C6 alkyl group, a dialkylamino group having two C1–C6 alkyl groups which may be identical to or different from each other, a hydroxyl group, a halogen atom, a C2–C6 perfluoroalkyl group, a cyano group, a nitro group, a carboxyl group, an alkoxycarbonyl group formed of a C1–C6 alkoxyl group and a carbonyl group, a tetrazolyl group, a sulfamoyl group, a methylenedioxy group, an ethylenedioxy group, a morpholinosulfonyl group, a piperazinosulfonyl group, a 4-alkylpiperazinosulfonyl group having a C1–C6 alkyl group, a 4-dialkylaminopiperidino group having at the 4-position a dialkylamino group having two C1–C6 alkyl groups which may be identical to or different from each other, a 4-monoalkylaminopiperidino group having a C1–C6 alkyl group, or a 4-aminopiperidino group.

Examples the nitrogen-containing bicyclic heterocyclic groups serving as substituents R include groups having a structure represented by the following formula:

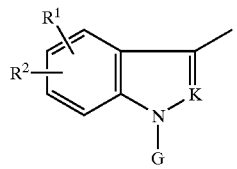

wherein the substituent G has the same meaning as described above; each of $R^1$ and $R^2$, which may be identical to or different from each other, represents a group selected from among a C1–C6 alkyl group, a C1–C6 alkoxyl group, a trifluoromethyl group, a 2,2,2-trifluoroethyl group, a trifluoromethoxyl group, a 2,2,2-trifluoroethoxyl group, a C1–C6 alkylthio group, a C1–C6 alkylsulfinyl group, a C1–C6 alkylsulfonyl group, an alkanoyl group formed of a C1–C6 alkylene group and a carbonyl group, a C2–C7 alkanoyloxy group, a C2–C7 alkanoylamino group, an amino group, a monoalkylamino group having a C1–C6 alkyl group, a dialkylamino group having two C1–C6 alkyl groups which may be identical to or different from each other, a hydroxyl group, a halogen atom, a C2–C6 perfluoroalkyl group, a cyano group, a nitro group, a carboxyl group, an alkoxycarbonyl group formed of a C1–C6 alkoxyl group and a carbonyl group, a tetrazolyl group, a sulfamoyl group, a methylenedioxy group, an ethylenedioxy group, a morpholinosulfonyl group, a piperazinosulfonyl group, a 4-alkylpiperazinosulfonyl group having a C1–C6 alkyl group, a 4-dialkylaminopiperidino group having at the 4-position a dialkylamino group having two C1–C6 alkyl groups which may be identical to or different from each other, a 4-monoalkylaminopiperidino group having a C1–C6 alkyl group, or a 4-aminopiperidino group; and K represents N (nitrogen atom), C (carbon atom), or C=O (carbonyl group), and the substituent G may be bonded to the 2-position of indazole. Examples of the phenyl group serving as R include groups having a structure represented by the following formula:

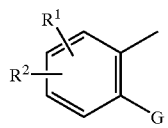

wherein $R^1$, $R^2$, and G have the same meanings as described above.

Examples of the nitrogen-containing bicyclic heterocyclic groups having a preferable structure include groups represented by the following formula:

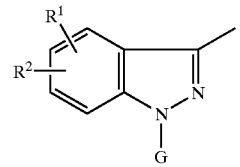

wherein the substituent G may be bonded to the 2-position of indazole. An indazole structure or a phenyl group structure is preferred as the substutuent R. Of these an indazole structure is more preferred.

When the substituent R is an indazole, examples of the substituent G connecting with the substituent R include groups which are already defined above as G and are selected from among the following:

a C1–C6 alkyl group, a phenyl group which may have a substituent, a benzoyl group which may have a substituent in the phenyl group portion, a benzylcarbonyl group which may have a substituent in the phenyl group portion, a benzoylmethyl group which may have a substituent in the phenyl group portion, an α-hydroxybenzyl group which may have a substituent in the phenyl group portion, a 6-membered aromatic heterocyclic group which may have a substituent and which contains one or two nitrogen atoms, a heterocyclic group-substituted alkylene group formed of a C1–C3 alkylene group and a 5-membered aromatic heterocyclic group, which 5-membered aromatic heterocyclic group may have a substituent and contains as a heteroatom a nitrogen atom, a sulfur atom, or an oxygen atom, a heterocyclic group-substituted alkyl group formed of a C1–C3 alkylene group and a 5-membered aromatic heterocyclic group, which 5-membered aromatic heterocyclic group may have a substituent and contains one nitrogen atom and as a second heteroatom a nitrogen atom, a sulfur atom, or an oxygen atom, a heterocyclic group-substituted alkyl group formed of a C1–C3 alkylene group and a 5-membered aromatic heterocyclic group, which 5-membered aromatic heterocyclic group may have a substituent and contains two nitrogen atoms and as a second heteroatom a nitrogen atom, a sulfur atom, or an oxygen atom, a heterocyclic group-substituted alkyl group formed of a C1–C3 alkylene group and a 6-membered aromatic heterocyclic group, which 6-membered aromatic heterocyclic group may have a substituent and contains one or two nitrogen atoms, a phenylhydroxyalkyl group formed of a C1–C3 alkylene group having one hydroxyl group and a phenyl group which may have a substituent, a 2-phenylethenyl group wherein its phenyl group may have a substituent, a C2–C7 alkanoylamino group, a tetrazolylalkyl group formed of a C1–C3 alkylene group and a tetrazolyl group wherein the alkylene group is bonded to a carbon atom or a nitrogen atom of the tetrazolyl group, a morpholinoalkyl group formed of a morpholino group and a C1–C3 alkylene group, an alkoxycarbonylalkyl group formed of a C1–C6 alkoxyl group, a carbonyl group, and a C1–C3 alkylene group, an 1-alkylindol-2-yl group wherein a C1–C6 alkyl group is bonded with the 1- position of indole which may have a substituent, a pyrrolidon-2-yl group which may have a substituent, a (2-guanidinothiazolyl)alkyl group formed of a 2-guanidinothiazolyl group and a C1–C3 alkylene group, a (4-alkylpiperazino)alkyl group formed of a C1–C6 alkylene group and a 4-alkylpiperazino group having a C1–C6 alkyl group at the 4-position of the piperazino group, a [4-(morpholinosulfonyl)phenyl]alkyl group formed of a C1–C6 alkylene group and a 4-(morpholinosulfonyl)phenyl group having a morpholinosulfonyl group at the 4-position of the phenyl group, a [4-(piperazinosulfonyl)phenyl]alkyl group formed of a C1–C6 alkylene group and a 4-(piperazinosulfonyl)phenyl group having a piperazinonosulfonyl group at the 4-position of the phenyl group, a [4-(4-alkylpiperazinosulfonyl)phenyl]alkyl group formed of a C1–C6 alkylene group and a 4-(4-alkylpiperazinosulfonyl)phenyl group wherein a 4-alkylpiperazinosulfonyl group having a C1–C6 alkyl group is bonded with the 4-position of the phenyl group, an alkoxycarbonylalkyl group formed of a C1–C6 alkoxyl group, a carbonyl group, and a C1–C6 alkylene group, a carboxylalkyl group formed of a carboxyl group and a C1–C6 alkylene group, a [4-(4-(dialkylaminopiperidino)phenyl]alkyl group formed of a C1–C6 alkylene group and a 4-(4-dialkylaminopiperidino)phenyl group wherein a 4-dialkylaminopiperidino group having, at the 4-position of piperidine, a dialkylamino group having C1–C6 alkyl groups which may be identical to or different from each other is bonded to the 4-position of the phenyl group, a [4-(4-(monoalkylaminopiperidino)phenyl]alkyl group formed of a C1–C6 alkylene group and a 4-(4-monoalkylaminopiperidino)phenyl group wherein a 4-monoalkylaminopiperidino group having, at the 4-position of piperidine, a monoalkylamino group having a C1–C6 alkyl group is bonded to the 4-position of the phenyl group, a [4-(4-aminopiperidino)phenyl]alkyl group formed of a C1–C6 alkylene group and a 4-(aminopiperidino)phenyl group wherein a 4-aminopiperidino group having, at the 4-position of piperidine, an amino group is bonded to the 4-position of the phenyl group, a (4-dialkylaminopiperidino)alkyl group formed of a C1–C6 alkylene group and a 4-dialkylaminopiperidino group wherein a dialkylamino group having two C1–C6 alkyl groups which may be identical to or different from each other is bonded to the 4-position of piperidine, a (4-monoalkylaminopiperidino)alkyl group formed of a C1–C6 alkylene group and a 4-monoalkylaminopiperidino group wherein a monoalkylamino group having a C1–C6 alkyl group is bonded to the 4-position of piperidine, a (4-aminopiperidino)alkyl group formed of a C1–C6 alkylene group and a 4-aminopiperidino group having an amino group at the 4-position of piperidine, a phenylalkyl group formed of a C1–C6 alkylene group and a phenyl group which may have a substituent, and a hydrogen atom.

Of these, more preferable examples thereof include groups which are selected from the following group:

a heterocyclic group-substituted alkyl group formed of a C1–C3 alkylene group and a 5-membered aromatic heterocyclic group, which 5-membered aromatic heterocyclic group may have a substituent and contains as a heteroatom a nitrogen atom, a sulfur atom, or an oxygen atom, a heterocyclic group-substituted alkyl group formed of a C1–C3 alkylene group and a 5-membered aromatic heterocyclic group, which 5-membered aromatic heterocyclic group may have a substituent and contains one nitrogen atom and as a second heteroatom a nitrogen atom, a sulfur atom, or an oxygen atom, a heterocyclic group-substituted alkyl group formed of a C1–C3 alkylene group and a 5-membered aromatic heterocyclic group, which 5-membered aromatic heterocyclic group may have a substituent and contains two nitrogen atoms and as a second heteroatom a nitrogen atom, a sulfur atom, or an oxygen atom, a heterocyclic group-substituted alkyl group formed of a C1–C3 alkylene group and a 6-membered aromatic heterocyclic group, which 6-membered aromatic heterocyclic group may have a substituent and contains one or two nitrogen atoms, tetrazolylalkyl, a (2-guanidinothiazolyl)alkyl group, a 1,4-dihydropyridyl group which may have a substituent, a [4-(morpholinosulfonyl)phenyl]alkyl group, a [4-(piperazinosulfonyl)phenyl]alkyl group, a [4-(4-alkylpiperazinosulfonyl)phenyl]alkyl group, an alkoxycarbonylalkyl group, a carboxylalkyl group, a [4-(4-dialkylaminopiperidino)phenyl]alkyl group, a [4-(4-monoalkylaminopiperidino)phenyl]alkyl group, a [4-(4-aminopiperidino)phenyl]alkyl group, a (4-dialkylaminopiperidino)alkyl group, a (4-monoalkylaminopiperidino)alkyl group, a (4-aminopiperidino)alkyl group, a phenylalkyl group, and a hydrogen atom.

When the substituent R contains an indazole group, particularly preferable substituent G connecting with the substituent R is a heterocyclic group-substituted alkyl group or a phenylalkyl group. A compound having a hydrogen atom serving as the substituent G is one of the preferable compounds in that it exhibits strong calmodulin-inhibition.

When the substituent R contains an indazole, preferable examples of the substituent G include an aralkyl group formed of an aryl group and a C1–C6 alkylene group. The aryl group contained in the aralkyl group includes a heterocyclic group derived from an aromatic heterocyclic compound as well as a substituent derived from an aromatic hydrocarbon compound. Examples of the aralkyl group include the following:

an α-hydroxybenzyl group, a heterocyclic group-substituted alkyl group formed of a C1–C3 alkylene group and a 5-membered aromatic heterocyclic group, which 5-membered aromatic heterocyclic group may have a substituent and contains as a heteroatom a nitrogen atom, a sulfur atom, or an oxygen atom, a heterocyclic group-substituted alkyl group formed of a C1–C3 alkylene group and a 5-membered aromatic heterocyclic group, which 5-membered aromatic heterocyclic group may have a substituent and contains one nitrogen atom and as a second heteroatom a nitrogen atom, a sulfur atom, or an oxygen atom, a heterocyclic group-substituted alkyl group formed of a C1–C3 alkylene group and a 5-membered aromatic heterocyclic group, which 5-membered aromatic heterocyclic group may have a substituent and contains two nitrogen atoms and as a second heteroatom a nitrogen atom, a sulfur atom, or an oxygen atom, a heterocyclic group-substituted alkyl group formed of a C1–C3 alkylene group and a 6-membered aromatic heterocyclic group, which 6-membered aromatic heterocyclic group may have a substituent and contains one or two nitrogen atoms, a phenylhydroxyalkyl group formed of a C2–C3 alkylene group having one hydroxyl group and a phenyl group which may have a substituent, a 2-phenylethenyl group wherein its phenyl group may have a substituent, a tetrazolylalkyl group formed of a C1–C3 alkylene group and a tetrazolyl group wherein the alkylene group is bonded to a carbon atom or a nitrogen atom of the tetrazolyl group, a morpholinoalkyl group formed of a morpholino group and a C1–C3 alkylene group, a (2-guanidinothiazolyl)alkyl group formed of a 2-guanidinothiazolyl group and a C1–C3 alkylene group, a [4-(morpholinosulfonyl)phenyl]alkyl group formed of a C1–C6 alkylene group and a 4-(morpholinosulfonyl)phenyl group having a morpholinosulfonyl group at the 4-position of the phenyl group, a [4-(piperazinosulfonyl)phenyl]alkyl group formed of a C1–C6 alkylene group and a 4-(piperazinosulfonyl)phenyl group having a piperazinonosulfonyl group at the 4-position of the phenyl group, a [4-(4-alkylpiperazinosulfonyl)phenyl]alkyl group formed of a C1–C6 alkylene group and a 4-(4-alkylpiperazinosulfonyl)phenyl group wherein a 4-alkylpiperazinosulfonyl group having a C1–C6 alkyl group is bonded with the 4-position of the phenyl group, a [4-(4-(dialkylaminopiperidino)phenyl]alkyl group formed of a C1–C6 alkylene group and a 4-(4-dialkylaminopiperidino)phenyl group wherein a 4-dialkylaminopiperidino group having, at the 4-position of piperidine, a dialkylamino group having C1–C6 alkyl groups which may be identical to or different from each other is bonded to the 4-position of the phenyl group, a [4-(4-(monoalkylaminopiperidino)phenyl]alkyl group formed of a C1–C6 alkylene group and a 4-(4-monoalkylaminopiperidino)phenyl group wherein a 4-monoalkylaminopiperidino group having, at the 4-position of piperidine, a monoalkylamino group having a C1–C6 alkyl group is bonded to the 4-position of the phenyl group, a [4-(4-(aminopiperidino)phenyl]alkyl group formed of a C1–C6 alkylene group and a 4-(4-aminopiperidino)phenyl group wherein a 4-aminopiperidino group having, at the 4-position of piperidine, an amino group is bonded to the 4-position of the phenyl group, and a phenylalkyl group formed of a C1–C6 alkylene group and a phenyl group which may have a substituent.

Among these aralkyl groups, an aralkyl group having a C1 or C2 alkylene group is preferred, and that having a C1 alkylene group, i.e., an arylmethyl group, is more preferred. As mentioned above, the aryl group also includes a heterocyclic aryl group in addition to a hydrocarbonic aryl group.

When the substituent R contains an indazole, the indazole may have a substituent. As mentioned above, examples of the preferable substituent include groups selected from among the following groups:

a C1–C6 alkoxyl group, a trifluoromethoxyl group, a 2,2,2-trifluoroethoxyl group, a C1–C6 alkylthio group, a C1–C6 alkylsulfinyl group, a C1–C6 alkylsulfonyl group, an alkanoyl group formed of a C1–C6 alkyl group and a carbonyl group, a C2–C7 alkanoylamino group, a monoalkylamino group having a C1–C6 alkyl group, a dialkylamino group wherein each of the alkyl groups is a C1–C6 alkyl group, a hydroxyl group, a halogen atom, a carboxyl group, an alkoxycarbonyl group formed of a C1–C6 alkoxyl group and a carbonyl group, a tetrazolyl group, a sulfamoyl group, a methylenedioxy group, an ethylenedioxy group, a morpholinosulfonyl group, a piperazinosulfonyl group, a 4-alkylpiperazinosulfonyl group having a C1–C6 alkyl group, a 4-(dialkylamino)piperidino group having a dialkylamino group having C1–C6 alkyl groups which may be identical to or different from each other, a 4-(monoalkylamino)piperidino group having a C1–C6 alkyl group, and a 4-aminopiperidino group.

When the substituent R contains an indazole, still more preferable examples thereof include groups selected from among the following groups:

a C1–C6 alkoxyl group, a trifluoromethoxyl group, a 2,2,2-trifluoroethoxyl group, a hydroxyl group, a halogen atom, preferably a fluorine atom, a tetrazolyl group, a sulfamoyl group, a methylenedioxy group, an ethylenedioxy group, a morpholinosulfonyl group, a piperidinosulfonyl group, a 4-alkylpiperazinosulfonyl group having C1–C6 alkyl group, a 4-(dialkylamino)piperidino group wherein each alkyl group is independently a C1–C6 alkyl group, a 4-(monoalkylamino)piperidino group having C1–C6 alkyl group, and a 4-aminopiperidino group.

Of these, when the substituent R includes an indazole, more preferred are:

a C1–C6 alkoxyl group, a sulfamoyl group, a methylenedioxy group, and an ethylenedioxy group.

Meanwhile, when the substituent R is a phenyl group, preferred examples of the substituent G connecting with the phenyl group include groups selected from among the following:

a phenyl group which may have a substituent, a 5-membered aromatic heterocyclic group which may have a substituent and which contains as a heteroatom a nitrogen atom, a sulfur atom, or an oxygen atom, a 5-membered aromatic heterocyclic group which may have a substituent and which contains one nitrogen atom and as a second heteroatom a nitrogen atom, a sulfur atom, or an oxygen atom, a 5-membered aromatic heterocyclic group which may have a substituent and which contains two nitrogen atoms and as a second heteroatom a nitrogen atom, a sulfur atom, or an oxygen atom, a 6-membered aromatic heterocyclic group which may have a substituent and which contains one or two nitrogen atoms, a tetrazolyl group, a morpholinoalkyl group consisting of a morpholino group and a C1–C3 alkylene group, an 1-alkylindol-2-yl group which has a C1–C6 alkyl group and which may further have a substituent, an 1,4-dihydropyridyl group which may have a substituent, and a 2-guanidinothiazolyl group.

When the substituent R is a phenyl group, an aryl group is preferred with regard to the substituent G connecting with the substituent R. Similarly, as mentioned above, the aryl group also includes a heterocyclic aryl group in addition to a hydrocarbonic aryl group.

When the substituent R is a phenyl group, the phenyl group may have one or more substituents. Examples of the preferable substituents include the same groups as described in the case in which the substituent R contains an indazole.

Examples of the preferable structures as the substituent R include an indazole structure having two methoxyl groups or a methylenedioxy group or a phenyl group structure having two methoxyl groups or a methylenedioxy group.

Among the groups as described above as the substituent Q, an aryl group is preferred. A phenyl group is preferred as the aryl group. The phenyl group may have one or more substituents. The phenyl group is preferably substituted at a m-position, which is defined to the bonding site of the phenyl group with piperazine. A halogen atom is preferable for the meta substituent, with a chlorine atom and a trifluoromethyl group being more preferable. When the meta substituent is a halogen atom, the phenyl group may have an alkyl group as a second substituent, whereas when it is a trifluoromethyl group, the phenyl group may have an alkoxyl group as a second substituent.

The present inventors think that, as the substituents connecting with the phenyl group, an electron-withdrawing substituent is suitable for the meta substituent, and an electron-donating group is suitable for the second substituent.

With regard to the bonding moiety Z between the substituent R and piperazine, an alkylene group is preferred among the above-described groups. A C2 or C3 alkylene group is preferred, with the C2 alkylene group being more preferred.

A typical example of a salt of the piperazine derivative (I) is an acid-adduct-type salt. The acid which is added in order to produce the salt may both be an inorganic acid and an organic acid. Examples of the inorganic acid include hydrochloric acid, sulfuric acid, nitric acid, and phosphoric acid. Carboxylic acids and sulfonic acids may be used as the organic acid, and examples thereof include acetic acid, propionic acid, lactic acid, maleic acid, fumaric acid, and methanesulfonic acid, benzenesulfonic acid, and toluenesulfonic acid, respectively. It is apparent that a compound of the piperazine derivative (I) can be used in the human body so long as the acid which forms the acid-adduct-type salt is harmless to the human body.

It is also apparent that when the piperazine derivative (I) contains an acidic moiety such as a carboxylic group or a sulfonyl group, the derivative can form a salt with a base via the acidic moiety.

In addition to the above-described adduct-type salt, the piperazine derivative (I) may take a hydrate form or a solvated form. The hydrate and the solvate include both that of the free compound of the formula (I) and a salt of the compound of the formula (I). They also include a tautomer of the compound of the formula (I).

Preferable examples of the piperazine derivative (I) include the following compounds:

3-[2-[4-(3-chloro-2-methylphenyl)-1-piperazinyl]ethyl]-5,6-dimethoxy-1-(3,4-dimethoxybenzyl)-1H-indazole or salts thereof 3-(2-(4-(3-chloro-2-methylphenyl)-1-piperazinyl)ethyl)-5,6-methylenedioxy-1-(3,4-dimethoxybenzyl)-1H-indazole or salts thereof, 3-(2-(4-(3-chloro-2-methylphenyl)-1-piperazinyl)ethyl)-5,6-dimethoxy-1-(4-imidazolylmethyl)-1H-indazole or salts thereof, 3-(2-(4-(3-chloro-2-methylphenyl)-1-piperazinyl)ethyl)-5,6-methylenedioxy-1-(4-imidazolylmethyl)-1H-indazole or salts thereof, 3-(2-(4-(3-chloro-2-methylphenyl)-1-piperazinyl)ethyl)-5,6-dimethoxy-1-(2-pyridylmethyl)-1H-indazole or salts thereof, 3-(2-(4-(3-chloro-2-methylphenyl)-1-piperazinyl)ethyl)-5,6-methylenedioxy-1-(2-pyridylmethyl)-1H-indazole or salts thereof, 3-(2-(4-(3-chloro-2-methylphenyl)-1-piperazinyl)ethyl)-5,6-dimethoxy-1-(3-pyridylmethyl)-1H-indazole or salts thereof, 3-(2-(4-(3-chloro-2-methylphenyl)-1-piperazinyl)ethyl)-5,6-methylenedioxy-1-(3-pyridylmethyl)-1H-indazole or salts thereof, 3-(2-(4-(3-chloro-2-methylphenyl)-1-piperazinyl)ethyl)-5,6-dimethoxy-1-(4-pyridylmethyl)-1H-indazole or salts thereof, 3-(2-(4-(3-chloro-2-methylphenyl)-1-piperazinyl)ethyl)-5,6-methylenedioxy-1-(4-pyridylmethyl)-1H-indazole or salts thereof, 3-[2-[4-(3-chloro-6-methoxyphenyl)-1-piperazinyl]ethyl]-5,6-dimethoxy-1-(3,4-dimethoxybenzyl)-1H-indazole or salts thereof, 3-(2-(4-(3-chloro-6-methoxyphenyl)-1-piperazinyl) ethyl)-5,6-methylenedioxy-1-(3,4-dimethoxybenzyl)-1H-indazole or salts thereof, 3-[2-[4-(3-trifluoromethylphenyl)-1-piperazinyl]ethyl]-5,6-dimethoxy-1-(3,4-dimethoxybenzyl)-1H-indazol or salts thereof, 3-(2-(4-(3-trifluoromethylphenyl)-1-piperazinyl)ethyl)-5,6-methylenedioxy-1-(3,4-dimethoxybenzyl)-1H-indazol or salts thereof, 5,6-dimethoxy-2-[[4,5-dimethoxy-2-[4-(2-methoxyphenyl)-1-piperazinyl]ethyl]phenyl]-1-methylindole or salts thereof, 5,6-dimethoxy-2-[[4,5-methylenedioxy-2-[4-(2-methoxyphenyl)-1-piperazinyl]ethyl]phenyl]-1-methylindole or salts thereof, 1-(3-chloro-2-methylphenyl)-4-[2-[[4,5-dimethoxy-2-(3,4-dimethoxyphenyl)]phenyl]ethyl]piperazine or salts thereof, 1-(3-chloro-2-methylphenyl)-4-[2-[[4,5-methylenedioxy-2-(3,4-dimethoxyphenyl)]phenyl]ethyl]piperazine or salts thereof, 3-[2-[4-(3-chloro-2-methylphenyl)-1-piperazinyl] propyl]-5,6-dimethoxy-1-(3,4-dimethoxybenzyl)-1H-indazole or salts thereof, 3-(2-(4-(3-chloro-2-methylphenyl)-1-piperazinyl) propyl)-5,6-methylenedioxy-1-(3,4-dimethoxybenzyl)-1H-indazole or salts thereof, 3-(2-(4-(3-chloro-2-methylphenyl)-1-piperazinyl) propyl)-5,6-dimethoxy-1-(4-imidazolylmethyl)-1H-indazole or salts thereof, 3-(2-(4-(3-chloro-2-methylphenyl)-1-piperazinyl) propyl)-5,6-methylenedioxy-1-(4-imidazolylmethyl)-1H-indazole or salts thereof, 3-(2-(4-(3-chloro-2-methylphenyl)-1-piperazinyl) propyl)-5,6-dimethoxy-1-(2-pyridylmethyl)-1H-indazole or salts thereof, 3-(2-(4-(3-chloro-2-methylphenyl)-1-piperazinyl) propyl)-5,6-methylenedioxy-1-(2.-pyridylmethyl)-1H-indazole or salts thereof, 3-(2-(4-(3-chloro-2-methylphenyl)-1-piperazinyl) propyl)-5,6-dimethoxy-1-(3-pyridylmethyl)-1H-indazole or salts thereof, 3-(2-(4-(3-chloro-2-methylphenyl)-1-piperazinyl) propyl)-5,6-methylenedioxy-1-(3-pyridylmethyl)-1H-indazole or salts thereof, 3-(2-(4-(3-chloro-2-methylphenyl)-1-piperazinyl) propyl)-5,6-dimethoxy-1-(4-pyridylmethyl)-1H-indazole or salts thereof, 3-(2-(4-(3-chloro-2-methylphenyl)-1-piperazinyl) propyl)-5,6-methylenedioxy-1-(4-pyridylmethyl)-1H-indazole or salts thereof, 3-[2-[4-(3-chloro-6-methoxyphenyl)-1-piperazinyl] propyl]-5,6-dimethoxy-1-(3,4-dimethoxybenzyl)-1H-indazole or salts thereof, 3-(2-(4-(3-chloro-6-methoxyphenyl)-1-piperazinyl) propyl)-5,6-methylenedioxy-1-(3,4-dimethoxybenzyl)-1H-indazole or salts thereof, 3-[2-[4-(3-trifluoromethylphenyl)-1-piperazinyl]propyl]-5,6-dimethoxy-1-(3,4-dimethoxybenzyl)-1H-indazole or salts thereof, 3-(2-(4-(3-trifluoromethylphenyl)-1-piperazinyl)propyl)-5,6-methylenedioxy-1-(3,4-dimethoxybenzyl)-1H-indazole or salts thereof, 5,6-dimethoxy-2-[[4,5-dimethoxy-2-[4-(2-methoxyphenyl)-1-piperazinyl]propyl]phenyl]-1-methylindole or salts thereof, 5,6-dimethoxy-2-[[4,5-methylenedioxy-2-[4-(2-methoxyphenyl)-1-piperazinyl]propyl]phenyl]-1-methylindole or salts thereof, 1-(3-chloro-2-methylphenyl)-4-[2-[[4,5-dimethoxy-2-(3,4-dimethoxyphenyl)]phenyl]propyl]piperazine or salts thereof, and 1-(3-chloro-2-methylphenyl)-4-[2-[[4,5-methylenedioxy-2-(3,4-dimethoxyphenyl)]phenyl]propyl]piperazine or salts thereof.

Of these, more preferable example includes the folowing compounds:

3-[2-[4-(3-chrolo-2-methylphenyl)-1-piperazinyl]ethyl]-5,6-dimethoxy-1-(3,4-dimethoxybenzyl)-1H-indazole or salts thereof and 3-(2-(4-(3-chrolo-2-methylphenyl)-1-piperazinyl)ethyl)-5,6-dimethoxy-1-(4-imidazolylmethyl)-1H-indazole or salts thereof.

With regard to the salt, 3-(2-(4-(3-chrolo-2-methylphenyl)-1-piperazinyl)ethyl)-5,6-dimethoxy-1-(4-imidazolylmethyl)-1H-indazole dihydrochloride 3.5 hydrate and 3-(2-(4-(3-chrolo-2-methylphenyl)-1-piperazinyl)ethyl)-5,6-dimethoxy-1H-indazole or salts thereof are particularly preferred.

The piperazine derivative (I) may be produced through a method described in, for example, Japanese Patent Application Laid-Open (kokai) No. 7-97364.

The water-soluble cyclodextrin derivative which is used in the present invention refers to a derivative having water solubility greater than that of β-cyclodextrin. Examples of the derivative include compounds represented by formula (II):

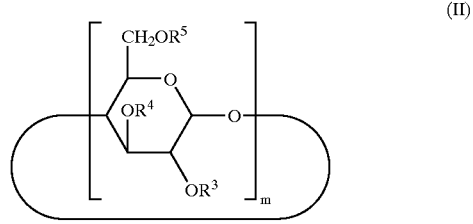

wherein m represents an integer between 6 and 12 inclusive and each of $R^3$, $R^4$, and $R^5$, which may be identical to or different from one another in each of the recurring units, represents a hydrogen atom, a sulfoalkyl group, a hydroxyalkyl group, or a sugar residue.

The variable m represents an integer between 6 and 12 inclusive, preferably between 6 and 9 inclusive, particularly 7, i.e., a β-cyclodextrin derivative.

Among $R^3$, $R^4$, and $R^5$, preferable examples of the sulfoalkyl group include sulfoalkyl groups having a C1–C6 alkyl group such as a sulfomethyl group, a sulfoethyl group, a sulfopropyl group, or a sulfobutyl group, with a sulfobutyl group being particularly preferable.

Preferable examples of the hydroxyalkyl group include hydroxyalkyl groups having a C1–C6 alkyl group such as a hydroxymethyl group, a hydroxyethyl group, a hydroxypropyl group, or a hydroxybutyl group, with a hydroxypropyl group being particularly preferable.

With regard to the sugar residue, sugar residues having 3–24 carbon atoms are preferred, and those having 6–12 carbon atoms are particularly preferred. Examples of the residue include a glucosyl group, a galactosyl group, a glycero-gluco-heptosyl group, a maltosyl group, and a lactosyl group, with a maltosyl group being more preferred.

The water-soluble cyclodextrin derivative represented by formula (II) has a substitution ratio, i.e., a ratio of a substituent other than a hydrogen atom to the sum of $R^3$, $R^4$, and $R^5$ in the water-soluble cyclodextrin derivative represented by formula (II), of preferably 70% or less, particularly preferably 20–50%.

With regard to the water-soluble cyclodextrin derivative, there may also be used suitable cyclodextrins described in, for example, Japanese Kohyo Patent Publication Nos. 5-504783 (WO91/11172) and 6-511513 (WO94/02518).

Examples of the water-soluble cyclodextrin derivative include sulfobutylcyclodextrin, hydroxypropylcyclodextrin, maltosylcyclodextrin, and salts thereof. In particular, sulfobutyl-β-cyclodextrin, hydroxypropyl-β-cyclodextrin, maltosyl-β-cyclodextrin, and salts thereof are preferred.

Furthermore, of these, sulfobutyl-β-cyclodextrin or hydroxypropyl-β-cyclodextrin and salts thereof having a substitution ratio of 70% or less, particularly 20–50% are preferred, and a β-cyclodextrin sulfobutylether sodium salt having a substitution ratio of approximately 33% and hydroxypropyl-β-cyclodextrin having a substitution ratio of approximately 23% are more preferred.

The piperazine-cyclodextrin complex of the present invention may be obtained by producing an aqueous solution containing the piperazine derivative (I) or a salt thereof and a water-soluble cyclodextrin derivative. The freely water-soluble cyclodextrin derivative is used in an amount of preferably one mol or more based on one mol of the piperazine derivative (I) or a salt thereof, particularly preferably 1–10 mol. The higher the concentration of the water-soluble cyclodextrin derivative, the more the solubility of the piperazine derivative (I) increases. No particular limitation is imposed on the method for producing the aqueous solution, and for example it is produced by use of water or a buffer in a temperature range approximately from –5 to 35° C.

The thus-obtained piperazine-cyclodextrin complex of the present invention may be used as such or in a powder form which is obtained by removing co-existing water. Examples of the method for removing water include lyophilization and drying under reduced pressure. A powder product obtained from lyophilization is particularly preferred.

The piperazine-cyclodextrin complex of the present invention exhibits its effects through either oral administration or parenteral administration, and it is preferably formed into a formulation for parenteral administration, particularly an injection formulation.

The dose of the complex of the present invention may be modified appropriately in accordance with the age, body weight, and severity of the patient's symptom. When the complex is administered perorally, the daily dose for an adult, reduced as the piperazine derivative (I), is 1 mg to 1000 mg, preferably 10 mg to 500 mg, and the complex may be administered at a single time or in a divided manner. Examples of the form of formulation include tablets, capsules, powders, and granules. These may be produced through a known technique by use of typical additives such as excipients, lubricants, and binders.

When the complex is administered parenterally, the daily dose for an adult, reduced as the piperazine derivative (I), is 1 mg to 500 mg, preferably 10 mg to 200 mg, and preferably, the complex is administered at the dose through hypodermic injection, intravenous injection or intravenous drip.

The piperazine-cyclodextrin complex of the present invention exhibits excellent calmodulin-inhibition and has excellent antihypoxia action. Moreover, it exhibits excellent efficacy against a variety of pathologic models (such as inhibition to late neurocyte death or antiedemic action of jirds) through peroral and parenteral administration at a dose which causes no central inhibition.

Accordingly, the piperazine-cyclodextrin complex of the present invention serves as an inhibitor for calmodulin-induced physiological action caused by intracellar calcium, and is useful as a therapeutic agent, particularly as a therapeutic agent and a preventive agent for a variety of diseases induced by excessive activation of calmodulin such as hypertension and ischemic diseases of the brain, heart, and kidney such as cerebral infarction, cerebral embolism, transient ischemic attack, cerebral thrombosis, cardiac infarction, angina pectoris, cardiac failure, acute renal failure, or nephritis; diseases of the brain region such as Alzheimer's disease, Parkinson disease, or Binswanger's disease; drug intoxication; gassing; traumatic brain diseases and diseases caused thereby such as aspontaneity, depression, or memory disorder. Moreover, the complex is particularly useful as a therapeutic agent for circulatory diseases and brain diseases or as a brain-protective agent.

EXAMPLES

The present invention will next be described by way of examples, but the present invention should not be construed as being limited thereto.

Example 1

To an aqueous solution of a β-cyclodextrin sulfobutyl ether sodium salt (product of CyDex; hereinafter may be abbreviated as SBE7-β-CD; molecular weight 2162.01; substitution ratio: 7/21 (about 33%)) (26, 40, or 72 mM; 2.5 ml) was added an excessive amount of 3-[2-[4-(3-chloro-2-methylphenyl)-1-piperadinyl]ethyl]-5,6-dimethoxy-1-(4-imidazolylmethyl)-1H-indazole,.2HCl.3.5H$_2$O(hereinafter may be abbreviated as compound (1); molecular weight: 631.0) (400 mg). The mixture was allowed to stand for 7 days in a 25° C. water bath. During the standing period, the mixture was sonicated once a day for 15 minutes, followed by stirring for 2 minutes. On the first, fifth, and seventh days, pH of the mixture was adjusted to 4.0 by addition of adequate amount of HCl. After pH was adjusted on the seventh day, the amount of the entirety of the mixture was adjusted to 5 ml (to thereby achieve a SBE7-β-CD concentration of 15, 20, or 30 mM). Six days later, the mixture was subjected to centrifugal separation, to thereby collect a supernatant. The supernatant was filtered through a 0.22 μm filter, and the concentration of the compound (1) contained in the filtrate was quantitatively determined by high performance liquid chromatography (HPLC) under the following conditions. Similarly, the solubility of the piperazine derivative (I) for water was also determined by HPLC. The results are shown in Table 1.

(Conditions for High Performance Liquid Chromatography (HPLC))

Column: Intersil ODS-2

Mobile phase: 50 mM phosphate buffer solution (pH 5.5)/acetonitrile (1:1)

Column temperature: 40° C.
Flow rate: 1.0 ml/min
Wavelength: 210 nm

TABLE 1

|  | Concentration of compound (1) in supernatant |
|---|---|
| SBE7-β-CD 13 mM | 19.0 mM |
| SBE7-β-CD 20 mM | 25.6 mM |
| SBE7-β-CD 36 mM | 56.7 mM |
| Compound (1) alone | 14.6 mM |

As is apparent from Table 1, the solubility of compound (1) is improved when SBE7-β-CD is added to form a complex and when the concentration of SBE7-β-CD is increased.

In this connection, formation of a complex was confirmed through visual observation of the Cotton effect. Briefly, whereas the CD (circular dichroism) spectrum of a solution containing the compound (1) alone shows a simple curve, when a cyclodextrin solution was added thereto, a negative Cotton effect was observed in the vicinity of 245 nm. The Cotton effect is known to be obtained only when a guest molecule is included in the intramolecular cavity of cyclodextrin ("Rotatory Dispersion—Its Application to Organic Chemistry," authored by Carldjerassi, translated by Koji NAKANISHI and Futaba YAMAZAKI (Tokyo Kagaku Dojin). Thus, compound (1) was confirmed to be included in a cyclodextrin molecule to thereby form a complex.

Example 2

To 10 mM isotonic phosphate buffer solution (pH 6.0, 2 ml) containing SBE7-β-CD or hydroxypropyl-β-cyclodextrin (product of Nihon Shokuhin Kako; hereinafter may be abbreviated as HP-β-CD; molecular weight 1413; substitution ratio: 4.8/21 (about 23%)) at a different concentration and 0.6 mM compound (1) (concentration that permits complete hemolysis) was added a suspension (0.2 ml) of red blood cells suspension (5%). The mixture was maintained for 30 minutes at 37° C. After centrifugal separation (1000× g, 5 min), oxyhemoglobin and methohemoglobin contained in the supernatant were determined based on the absorbance at 588 nm, to thereby investigate the hemolysis activity of compound (1). The results are shown in FIG. 1.

When a complex was formed by the addition of SBE7-β-CD or HP-β-CD, the hemolysis activity of compound (1) was suppressed, and the higher the concentration of the cyclodextrin compound, the more the hemolysis activity was suppressed.

Example 3

An aqueous solution having a composition shown in Table 2 was prepared. The solution was subcutaneously injected to the back of a rat. Thirty minutes after injection, a 0.5% Evans blue solution was intravenously injected, and 30 minutes thereafter, the area of the skin in which the dye exuded was measured to check vascular permeability.

Figure 2:
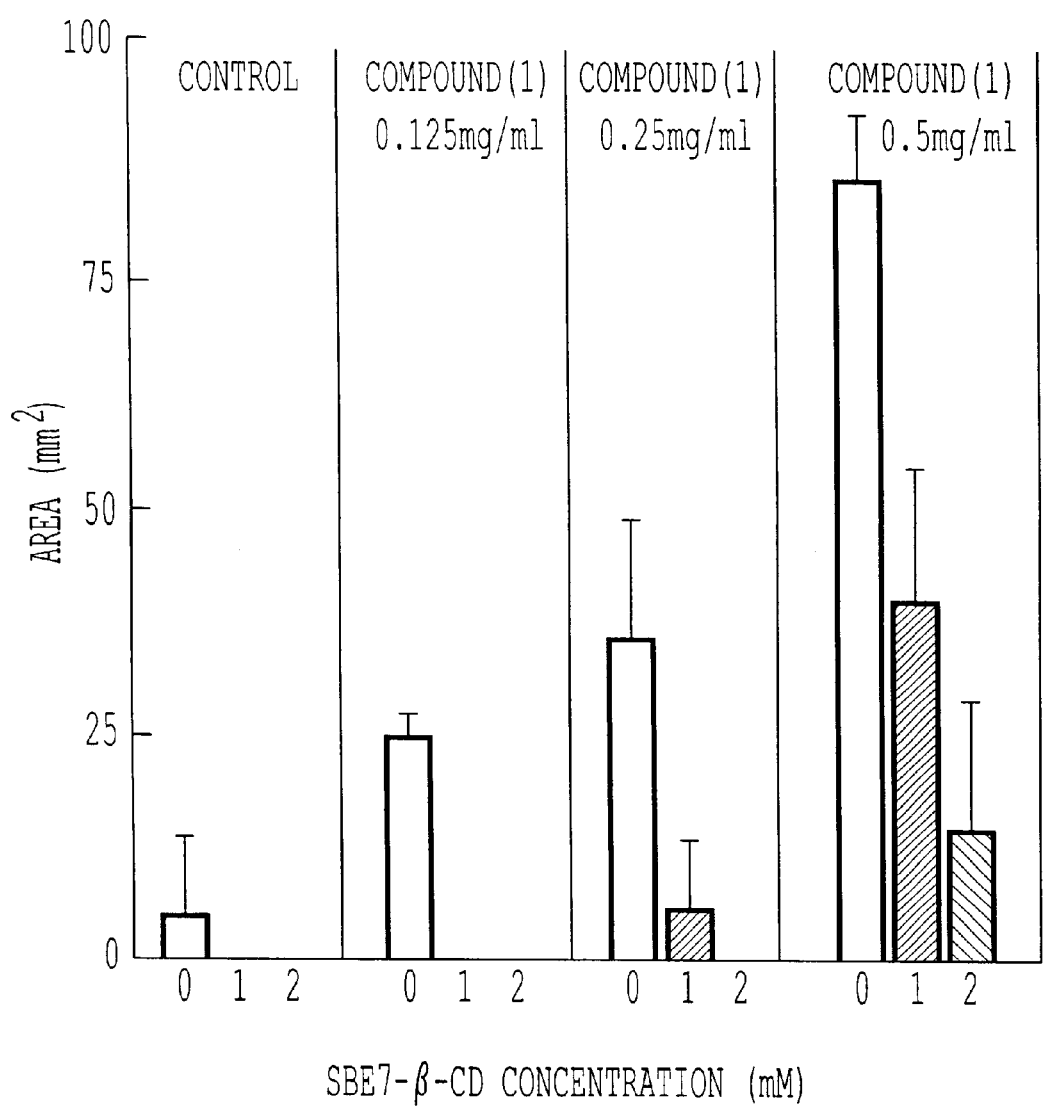
FIG. 2 is a graph showing vascular permeability (expressed by dye-exuded area) in the case in which in Example 3 SEB7-β-CD was added at a variety of concentrations.

FIG. 2 shows that the vascular permeability caused by complex compound (1) and SBE7-β-CD was lower than that of compound (1).

TABLE 2

| Concentration of compound (1) | Concentration of SBE7-β-CD* | | |
|---|---|---|---|
| 0 mg/mL | none (5.74) | 1 mM | 2 mM (5.73) |
| 0.125 mg/mL (0.25 mM) | none (5.55) | 1 mM | 2 mM |
| 0.25 mg/mL (0.51 mM) | none (5.39) | 1 mM | 2 mM (5.55) |
| 0.5 mg/mL (1.01 mM) | none (5.27) | 1 mM | 2 mM |

*Figures in ( ) represent pH.

Example 4

An aqueous solution having a composition shown in Table 3 was prepared, and 10 ml-aliquots were individually put into ampules. The solution was prepared as follows. The compound (1) (2.55 g) was dissolved in water for injection (700 ml). Independently, SBE7-β-CD (18.04 g) was dissolved in water for injection (200 ml), and the solutions were mixed. The pH was adjusted, and then water for injection was added so as to make the volume of the entirety equal to 1 liter.

The thus-obtained ampules were stored for 20 days under light of 2500 lux. Thereafter, the compound (1) content in each case was quantitatively determined by high performance liquid chromatography (HPLC) under the same conditions as used in Example 1.

The results, expressed as the residual ratio of compound (1), are also shown in Table 3.

TABLE 3

| Components (in one ampule) | Solution A | Solution B |
|---|---|---|
| Compound (1) | 25.5 mM[*1] | 25.5 mM[*1] |
| SBE7-β-CyD | 172.8 mM[*2] | — |
| Hydrochloric acid | appropriate[*3] | — |
| Water for injection | total 10 ml | total 10 ml |
| Ratio of residual compound (1) | 100.5% | 91.0% |

[*1]20.0 mg (4 mM), reduced as a free base anhydrate.
[*2]Corresponding to pH of 8.
[*3]To adjust pH to 4.0.

As is apparent from Table 3, the complex of the present invention is excellent in terms of stability against photolytic stress.

Example 5

Solutions A and B prepared in Example 4 were respectively diluted with a transfusion EL-1 (product of Morishita-Roussel) so that the concentration of compound (1) became 20 μg/ml. The solution was placed in a dripping tube (made of polyvinyl chloride) of a transfusion set, and stored for 2 hours under light-shielded conditions at 25° C. The compound (1) content of the diluted solution after storage was quantitatively determined by high performance liquid chromatography (HPLC) under the same conditions as described in Example 1.

The recovery rate of compound (1) was 102% for the case of solution A and 87% for the case of solution B. Thus, the complex of the present invention was proven to exhibit improved adsorption onto the transfusion set.

Industrial Applicability

The piperazine-cyclodextrin complexes of the present invention exhibit remarkably improved solubility as compared with the case of a sole use of piperazine derivative (I). Also, they suppress hemolysis activity and vascular permeability, and exhibit reduced local stimulation. Moreover, they exhibit excellent stability against photolytic stress and reduced adsorption onto the container therefor.

What is claimed is:

1. A piperazine-cyclodextrin complex formed of a piperazine derivative or a salt thereof and a freely water-soluble cyclodextrin derivative, wherein the piperazine derivative is represented by formula (I):

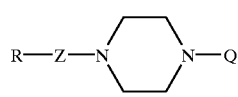

wherein
Q represents
(1) an aryl group,
(2) a heterocyclic group,
(3) a diarylmethyl group,
(4) an aralkyl group formed of an aryl group and a C1–C6 alkylene group,
(5) a C1–C8 alkyl group, or
(6) a C3–C8 cycloalkyl group, wherein each of the aryl group, the heterocyclic group, and the aryl groups in the diarylmethyl group and the aralkyl group may have one or more substituents selected from among the following groups:
1) a C1–C6 alkyl group,
2) a C1–C6 alkoxyl group,
3) a trifluoromethyl group and a 2,2,2-trifluoroethyl group,
4) a trifluoromethoxyl group and a 2,2,2-trifluoroethoxyl group,
5) a C1–C6 alkylthio group,
6) a C1–C6 alkylsulfinyl group,
7) a C1–C6 alkylsulfonyl group,
8) an alkanoyl group formed of a C1–C6 alkyl group and carbonyl group,
9) a C2–C7 alkanoyloxy group,
10) a C2–C7 alkanoylamino group,
11) an amino group,
12) a monoalkylamino group having a C1–C6 alkyl group,
13) a dialkylamino group wherein each of the alkyl groups is a C1–C6 alkyl group,
14) a hydroxyl group,
15) a halogen atom,
16) a C2–C6 perfluoroalkyl group,
17) a cyano group,
18) a nitro group,
19) a carboxyl group,
20) an alkoxycarbonyl group formed of a C1–C6 alkoxyl group and a carbonyl group,
21) a tetrazolyl group,
22) a sulfamoyl group,
23) a methylenedioxy group, an ethylenedioxy group, and propylenedioxy group,
24) a morpholinosulfonyl group,
25) a piperazinosulfonyl group,
26) a 4-alkylpiperazinosulfonyl group having a C1–C6 alkyl group,
27) a 4-(dialkylamino)piperidino group having a dialkylamino group having two C1–C6 alkyl groups which may be identical to or different from each other,
28) a 4-(monoalkylamino)piperidino group having a C1–C6 alkyl group, and
29) a 4-aminopiperidino group;

R represents a bicyclic nitrogen-containing heterocyclic group (i), wherein the nitrogen containing heterocyclic group has a condensed ring structure formed of a 5-membered ring and a 6-membered ring; one or two nitrogen atoms are contained in the 5-membered ring portion; the nitrogen-containing ring may be an aromatic or saturated ring; and the saturated ring may contain a ketone moiety; wherein the 5-membered ring portion of the bicyclic heterocyclic group (i) is substituted with substituent G selected from the group consisting of the following groups:
(aa) a C1–C6 alkyl group,
(ab) a phenyl group which may have a substituent,
(ac) a benzyl group which may have a substituent in the phenyl group portion,
(ad) a benzoyl group which may have a substituent in the phenyl group portion,
(ae) a benzylcarbonyl group which may have a substituent in the phenyl group portion,
(af) a benzoylmethyl group which may have a substituent the phenyl group portion,
(ag) an α-hydroxybenzyl group which may have a substituent in the phenyl group portion,
(ah) a 5-membered aromatic heterocyclic group which may have a substituent and which contains as a heteroatom a nitrogen atom, an oxygen atom, or a sulfur atom; wherein when the heteroatom is a nitrogen atom, the nitrogen atom is bonded to a hydrogen atom or to a C1–C6 alkyl group, or the nitrogen atom serves as the bonding site for the nitrogen-containing heterocyclic group or for the phenyl group,
(ai) a 5-membered aromatic heterocyclic group which may have a substituent and which contains as a heteroatom one nitrogen atom and as a second heteroatom a nitrogen atom, an oxygen atom, or a sulfur atom; wherein when the second heteroatom is a nitrogen atom, the nitrogen atom is bonded to hydrogen atom or to a C1–C6 alkyl group, or the nitrogen atom serves as the bonding site for the nitrogen-containing heterocyclic group or for the phenyl group,
(aj) a 5-membered aromatic heterocyclic group which may have a substituent and which contains as heteroatoms two nitrogen atoms and as a third heteroatom a nitrogen atom, an oxygen atom, or a sulfur atom; wherein when the third heteroatom is a nitrogen atom, the nitrogen atom is bonded to hydrogen atom or to a C1–C6 alkyl group, or the nitrogen atom serves as the bonding site for the nitrogen-containing heterocyclic group or for the phenyl group,
(ak) a 6-membered aromatic heterocyclic group which may have a substituent and which contains one or two nitrogen atoms,
(al) a heterocyclic group-substituted alkyl group formed of a C1–C3 alkylene group and a 5-membered aromatic heterocyclic group, which 5-membered aromatic heterocyclic group may have a substituent and contains as a heteroatom a nitrogen atom, an oxygen atom, or a sulfur atom; wherein when the heteroatom is a nitrogen atom, the nitrogen atom is bonded to a hydrogen atom or to a C1–C6 alkyl group, (am) a heterocyclic group-substituted alkyl group formed of a C1–C3 alkylene group and a 5-membered aromatic heterocyclic group, which 5-membered aromatic heterocyclic group may have a substituent and contains as a heteroatom one nitrogen atom and as a second heteroatom a nitrogen atom, an oxygen atom, or a sulfur atom; wherein when the second heteroatom is a nitrogen atom, the nitrogen atom is bonded to hydrogen atom or to a C1–C6 alkyl group, or the nitrogen atom serves as the bonding site for the alkylene group, (an) a heterocyclic group-substituted alkyl group formed of a C1–C3 alkylene group and a 5-membered aromatic heterocyclic group, which 5-membered aromatic heterocyclic group may have a substituent and contains as heteroatoms two nitrogen atoms and as a third heteroatom a nitrogen atom, an oxygen atom, or a sulfur atom; wherein when the third heteroatom is a nitrogen atom, the nitrogen atom is bonded to hydrogen atom or to a C1–C6 alkyl group, or the nitrogen atom serves as the bonding site for the alkylene group, (ao) a heterocyclic group-substituted alkyl group formed of a C1–C3 alkylene group and a 6-membered aromatic heterocyclic group which may have a substituent and which contains one or two nitrogen atoms, (ap) a phenylhydroxyalkyl group formed of a C2–C3 alkylene group having one hydroxyl group and a phenyl group which may have a substituent, (aq) a 2-phenylethynyl group wherein its phenyl group may have a substituent, (ar) a tetrazolyl group, (as) a morpholino group, (at) a C2–C7 alkanoylamino group, (au) a tetrazolylalkyl group formed of a tetrazolyl group and a C1–C3 alkylene group wherein the alkylene group bonded to the carbon atom or a nitrogen atom of the tetrazolyl group, (av) a morpholinoalkyl group formed of a morpholinoalkyl group and a C1–C3 alkylene group, (aw) a 4-alkoxycarbonylcyclohexyl group wherein its alkoxyl group has one to six carbon atoms, (ax) an alkoxycarbonyl group wherein its alkoxyl group has one to six carbon atoms, (ay) an alkoxycarbonylalkyl group formed of a C1–C3 alkylene group and an alkoxycarbonyl group wherein its alkoxyl group has one to six carbon atoms, (az) an 1-alkylindol-2-yl group wherein its alkyl group has one to six carbon atoms and the indole group may further have a substituent, (ba) a pyrrolidon-1-yl group, (bb) a 2-guanidinothiazolyl group, (bc) a (2-guanidinothiazolyl)-alkyl group formed of a guanidinothiazolyl group and a C1–C3 alkylene group, (bd) a 1,4-dihydropyridyl group which may have a substituent, (be) a 4-alkylpiperadinoalkyl group formed of a C1–C6 alkylene group and a 4-alkylpiperazino group having a C1–C6 alkyl group, (bf) a 4-(morpholinosulfonyl)phenylalkyl group formed of a 4-(morpholinosulfonyl)phenyl group and a C1–C6 alkylene group, (bg) a 4-(piperazinosulfonyl)phenylalkyl group formed a 4-(piperazinosulfonyl)phenyl group and a C1–C6 alkylene group, (bh) a 4-(piperazinosulfonyl)phenylalkyl group formed a C1–C6 alkylene group and a 4-(alkylpiperazinosulfonyl)phenyl group having a C1–C6 alkyl group, (bi) an alkoxycarbonylalkyl group formed of a C2–C7 alkoxycarbonyl group and a C1–C6 alkylene group, (bj) a carboxylalkyl group formed of a carboxyl group and a C1–C6 alkylene group, (bk) a [4-(4-dialkylaminopiperidino)phenyl]alkyl group formed of a C1–C6 alkylene group and a 4-(4alkylaminopiperidino)phenyl group wherein a 4-alkylaminopiperidino group having, at the 4-position of the piperidine, a dialkylamino group containing two C1–C6 alkyl groups is bonded to the 4-position of the phenyl group, (bl) a 4-(4-monoalkylaminopiperidino)phenylalkyl group formed of a C1–C6 alkylene group and a 4-(4noalkylaminopiperidino)phenyl group wherein a 4-monoalkylaminopiperidino group having, at the 4-position of the piperidine, a monoalkylamino group containing a C1–C6 alkyl group is bonded to the 4-position of the phenyl group, (bm) a [4-(4-aminopiperidino)phenyl]alkyl group formed a C1–C6 alkylene group and a 4-(4-aminopiperidino)phenyl group wherein a 4-aminopiperidino group is bonded to the 4-position of the phenyl group, (bn) a (4-dialkylaminopiperidino)alkyl group formed of C1–C6 alkylene group and a 4-dialkylaminopiperidino group wherein a dialkylamino group having two C1–C6 alkyl groups is bonded to the 4-position of the piperidine, (bo) a (4-mono alkyl aminopiperidino)alkyl group formed a C1–C6 alkylene group and a 4-monoalkylaminopiperidino group wherein a monoalkylamino group having a C1–C6 alkyl group is bonded to the 4-position of the piperidine, (bp) a (4-aminopiperidino)alkyl group formed of a 4-aminopiperidino group and a C1–C6 alkylene group, and (bq) a hydrogen atom, wherein when the substituents represented by (aa) through (az) have substituents, the substituents are one or more members selected from the group consisting of the following substituents:

1) a C1–C6 alkyl group,
2) a C1–C6 alkoxyl group,
3) a trifluoromethyl group and a 2,2,2-trifluoroethyl group,
4) a trifluoromethoxyl group and a 2,2,2-trifluoroethoxyl group,
5) a C1–C6 alkylthio group,
6) a C1–C6 alkylsulfinyl group,
7) a C1–C6 alkylsulfonyl group,
8) an alkanoyl group formed of a C1–C6 alkyl group and carbonyl group,
9) a C2–C7 alkanoyloxy group,
10) a C2–C7 alkanoylamino group,
11) an amino group,
12) a monoalkylamino group having a C1–C6 alkyl group,
13) a dialkylamino group wherein each of the alkyl groups is a C1–C6 alkyl group, 14) a hydroxyl group,
15) a halogen atom,
16) a C2–C6 perfluoroalkyl group,
17) a cyano group,
18) a nitro group,
19) a carboxyl group,
20) an alkoxycarbonyl group formed of a C1–C6 alkoxyl group and a carbonyl group,
21) a tetrazolyl group,
22) a sulfamoyl group,
23) a methylenedioxy group, an ethylenedioxy group, and propylenedioxy group,
24) a morpholinosulfonyl group,
25) a piperazinosulfonyl group,
26) a 4-alkylpiperazinosulfonyl group having a C1–C6 alkyl group,
27) a 4-(dialkylamino)piperidino group having a alkylamino group having two C1–C6 alkyl groups which may be identical to or different from each other,
28) a 4-(monoalkylamino)piperidino group having a C1–C6 alkyl group, and
29) a 4-aminopiperidyl group;
wherein the 6-membered ring portion of the bicyclic heterocyclic group (i) or the phenyl group (ii) may have one more groups selected from among a C1–C6 alkyl group, a C16 alkoxyl group, a trifluoromethyl group, a 2,2,2-trifluoroethyl group, a trifluoromethoxyl group, a 2,2,2-trifluoroethoxyl group, a C1–C6 alkylthio group, a C1–C6 alkylsulfinyl group, a C1–C6 alkylsulfonyl group, an alkanoyl group formed of a C1–C6 alkylene group and a carbonyl group, C2–C7 alkanoyloxy group, a C2–C7 alkanoylamino group, an amino group, a monoalkylamino group having a C1–C6 alkyl groups, a dialkylamino group having two C1-C6 alkyl groups which may be identical to or different from each other, a hydroxyl group, a halogen atom, a C2–C6 perfluoroalkyl group, cyano group, a nitro group, a carboxyl group, an alkoxycarbonyl group formed of a C1–C6 alkoxyl group and a carbonyl group, a tetrazolyl group, a sulfamoyl group, methylenedioxy group, an ethylenedioxy group, a morpholinosulfonyl group, a piperazinosulfonyl group, a 4-alkylpiperazinosulfonyl group having a C1–C6 alkyl group, a 4-dialkylaminopiperidino group having at the 4-position a dialkylamino group having two C1–C6 alkyl groups which may be identical to or different from each other, a 4-monoalkylaminopiperidino group having a C1–C6 alkyl group, or 4-aminopiperidino group;
and
Z represents
(1) a C1–C3 alkylene group,
(2) a C2–C4 alkenylene group,
(3) a C1–C3 alkylene group having one hydroxyl group,
(4) a carbonyl moiety,
(5) a C1–C2 alkylene group containing one carbonyl moiety at one end or an intermediate position of the carbon chain, or
(6) an oxalyl group.

2. The piperazine-cyclodextrin complex according to claim 1, wherein the piperazine derivative is 3-[2-[4-(3-chloro-2-methylphenyl)-1-piperazinyl]ethyl]-5,6-dimethoxy-1-(4-imidazolylmethyl)-1H-indazole or a salt thereof.

3. The piperazine-cyclodextrin complex according to claim 2, which is obtained through use of 3-[2-[4-(3-chloro-2-methylphenyl)-1-piperazinyl]ethyl]-5,6-dimethoxy-1-(4 imidazolylmethyl)-1H-indazole dihydrochloride 3.5 hydrate as the piperazine derivative.

4. The piperazine-cyclodextrin complex according to any one of claims 1 through 3, wherein the water-soluble cyclodextrin derivative is sulfobutylcyclodextrin or a salt thereof.

5. The piperazine-cyclodextrin complex according to any one of claims 1 through 3, wherein the water-soluble cyclodextrin derivative is sulfobutyl-β-cyclodextrin or a salt thereof.

6. The piperazine-cyclodextrin complex according to any one of claims 1 through 3, wherein the water-soluble cyclodextrin derivative is sulfobutyl-β-cyclodextrin having a substitution ratio of 70% or less, or a salt thereof.

7. The piperazine-cyclodextrin complex according to any one of claims 1 through 5, wherein the water-soluble cyclodextrin derivative is sulfobutyl-β-cyclodextrin having a substitution ratio of 20%–50%, or a salt thereof.

8. The piperazine-cyclodextrin complex according to any one of claims 1 through 3, wherein the water-soluble cyclodextrin derivative is β-cyclodextrin sulfobutyl ether sodium salt having a substitution ratio of about 33%.

9. The piperazine-cyclodextrin complex according to any one of claims 1 through 3, wherein the water-soluble cyclodextrin derivative is hydroxypropylcycledextrin or a salt thereof.

10. The piperazine-cyclodextrin complex according to any one of claims 1 through 3, wherein the water-soluble cyclodextrin derivative is hydroxypropyl-β-cyclodextrin or a salt thereof.

11. The piperazine-cyclodextrin complex according to any one of claims 1 through 3, wherein the water-soluble cyclodextrin derivative is hydroxypropyl-β-cyclodextrin having a substitution ratio of 70% or less, or a salt thereof.

12. The piperazine-cyclodextrin complex according to any one of claims 1 through 3, wherein the water-soluble cyclodextrin derivative is hydroxypropyl-β-cyclodextrin having a substitution ratio of 20–50%, or a salt thereof.

13. The piperazine-cyclodextrin complex according to any one of claims 1 through 3, wherein the water-soluble cyclodextrin derivative is hydroxypropyl-β-cyclodextrin having a substitution ratio of about 23%, or a salt thereof.

14. The piperazine-cyclodextrin complex according to any one of claims 1 through 3, wherein the water-soluble cyclodextrin derivative is maltosylcyclodextrin or a salt thereof.

15. The piperazine-cyclodextrin complex according to any one of claims 1 through 3, wherein the water-soluble cyclodextrin derivative is maltosyl-β-cyclodextrin or a salt thereof.

16. An injection formulation containing a piperazine-cyclodextrin complex as defined in any one of claims 1 through 3.

17. An injection formulation obtained through lyophilization of an aqueous solution containing a piperazine-cyclodextrin complex as defined in any one of claims 1 through 3.

18. A method for the treatment of circulatory diseases cerebral diseases, comprising administering a piperazine-cyclodextrin complex as defined in any one of claims 1 through 3 to a subject in need thereof.

19. A pharmaceutical composition, comprising the piperazine-cyclodextrin complex as defined in any one of claims 1 through 3 and a pharmaceutically acceptable carrier.

* * * * *

UNITED STATES PATENT AND TRADEMARK OFFICE
CERTIFICATE OF CORRECTION

PATENT NO. : 6,596,706 B1
DATED : July 22, 2003
INVENTOR(S) : Masahiko Kikuchi et al.

It is certified that error appears in the above-identified patent and that said Letters Patent is hereby corrected as shown below:

Column 30,
Line 28, "the phenyl group" should read -- of the phenyl group --.

Column 32,
Lines 1 and 4, "group formed" should read -- group formed of --;
Line 14, "4-(4alkylaminopiperidino)phenyl" should read -- 4-(4-alkylaminopiperidino) phenyl --;
Line 22, "4-(4noalkylaminopiperidino)phenyl" should read
-- 4-(4-moalkylaminopiperidino)phenyl --;
Line 28, "formed a" should read -- formed of a --;
Line 37, "(4-mono alkyl aminopiperidino)alkyl" should read
-- (4-monoalkylaminopiperidino)alkyl --.

Column 34,
Line 18, "claims 1 through 5," should read -- claims 1 through 3, --;
Line 27, "hydroxypropylcycledextrin" should read -- hydroxypropylcyclodextrin --.

Signed and Sealed this

Twenty-fifth Day of November, 2003

JAMES E. ROGAN
*Director of the United States Patent and Trademark Office*